(12) United States Patent
Scheller et al.

(10) Patent No.: US 11,364,066 B2
(45) Date of Patent: *Jun. 21, 2022

(54) IRRIGATING BIPOLAR FORCEPS

(71) Applicant: Kogent Surgical, LLC, Chesterfield, MO (US)

(72) Inventors: Gregg D Scheller, Wildwood, MO (US); Brett D Smith, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/697,052

(22) Filed: Apr. 27, 2015

(65) Prior Publication Data

US 2015/0374429 A1  Dec. 31, 2015

Related U.S. Application Data

(60) Provisional application No. 62/016,817, filed on Jun. 25, 2014.

(51) Int. Cl.
*A61B 17/28* (2006.01)
*A61B 18/14* (2006.01)
*A61B 18/00* (2006.01)

(52) U.S. Cl.
CPC ...... *A61B 18/1442* (2013.01); *A61B 18/1445* (2013.01); *A61B 2018/00029* (2013.01); *A61B 2018/00083* (2013.01); *A61B 2018/00107* (2013.01); *A61B 2018/00577* (2013.01); *A61B 2018/00589* (2013.01); *A61B 2018/1462* (2013.01); *A61B 2218/002* (2013.01)

(58) Field of Classification Search
None
See application file for complete search history.

(56) References Cited

U.S. PATENT DOCUMENTS

| 3,100,489 A | 8/1963 | Bagley |
| 4,567,890 A | 2/1986 | Ohta et al. |
| 5,647,871 A | 7/1997 | Levine et al. |
| 5,674,220 A | 10/1997 | Fox et al. |
| 6,050,996 A | 4/2000 | Schmaltz et al. |

(Continued)

FOREIGN PATENT DOCUMENTS

EP     17099232 A2    10/2006

OTHER PUBLICATIONS

Manuel Dujovny et al., Bipolar Jeweler's Forceps With Automatic Irrigation, for Coagulation in Microsurgery, Plastic and Reconstructive Surgery, 585-587, Nov. 1975.

(Continued)

*Primary Examiner* — Erica S Lee

(57) ABSTRACT

An irrigating bipolar forceps may include a first forceps arm, a conductor tip of the first forceps arm, a second forceps arm, a conductor tip of the second forceps arm, an input conductor isolation mechanism, and irrigation tubing. A proximal end of the first forceps arm may be disposed within the input conductor isolation mechanism and a proximal end of the second forceps arm may be disposed within the input conductor isolation mechanism. An application of a force to a lateral portion of the forceps arms may be configured to close the forceps arms. A reduction of a force applied to a lateral portion of the forceps arms may be configured to open the forceps arms. The irrigation tubing may transport a fluid from an irrigation supply system to a surgical site.

16 Claims, 11 Drawing Sheets

(56) References Cited

U.S. PATENT DOCUMENTS

| | | | |
|---|---|---|---|
| 6,228,084 | B1 | 5/2001 | Kirwan, Jr. |
| 6,231,574 | B1 | 5/2001 | Posthuma |
| 6,293,946 | B1 | 9/2001 | Thorne |
| 6,482,205 | B1 | 11/2002 | Bonnet |
| 6,679,881 | B1 | 1/2004 | Bybee |
| 6,749,610 | B2 | 5/2004 | Kirwan, Jr. et al. |
| 6,767,348 | B2 | 7/2004 | Nakada et al. |
| 6,860,882 | B2 | 3/2005 | Battles et al. |
| 6,863,669 | B2 | 3/2005 | Spitzer |
| 7,122,035 | B2 | 10/2006 | Canady |
| 7,150,097 | B2 | 12/2006 | Sremcich et al. |
| D559,984 | S | 1/2008 | Scheller |
| 7,402,754 | B2 | 7/2008 | Kirwan, Jr. et al. |
| 7,621,911 | B2 | 11/2009 | Ariola, Jr. |
| 7,736,361 | B2 | 6/2010 | Palanker et al. |
| 7,867,230 | B2 | 1/2011 | Asahara et al. |
| 7,963,965 | B2 | 6/2011 | Buysse et al. |
| 8,048,107 | B2 | 11/2011 | Chen |
| 8,083,735 | B2 | 12/2011 | Morris |
| 8,108,994 | B2 | 2/2012 | Ariola, Jr. et al. |
| 8,192,433 | B2 | 6/2012 | Johnson et al. |
| 8,211,105 | B2 | 7/2012 | Buysee et al. |
| 8,241,278 | B2 | 8/2012 | Sartor |
| 8,469,956 | B2 | 6/2013 | McKenna et al. |
| 2003/0139743 | A1* | 7/2003 | Spitzer ............... A61B 18/1442 606/51 |
| 2003/0181909 | A1* | 9/2003 | Kirwan, Jr. ........ A61B 18/1442 606/51 |
| 2005/0107784 | A1 | 5/2005 | Moses et al. |
| 2006/0217709 | A1 | 9/2006 | Couture et al. |
| 2006/0276785 | A1* | 12/2006 | Asahara ............. A61B 18/1442 606/51 |
| 2007/0255272 | A1* | 11/2007 | Ariola, Jr. .......... A61B 18/1442 606/41 |
| 2008/0200914 | A1 | 8/2008 | Hanlon et al. |
| 2012/0004653 | A1 | 1/2012 | Butsch |
| 2013/0023866 | A1* | 1/2013 | Stringham ........... A61B 18/082 606/29 |
| 2013/0066317 | A1 | 3/2013 | Evans et al. |
| 2014/0194870 | A1* | 7/2014 | Hanlon ............... A61B 18/1442 606/41 |
| 2014/0206987 | A1* | 7/2014 | Urbanski ............... A61M 5/007 600/424 |
| 2015/0005768 | A1* | 1/2015 | Sutherland ......... A61B 18/1442 606/42 |

OTHER PUBLICATIONS

Ananth K. Vellimana et al., Current Technological Advances of Bipolar Coagulation, Operative Neurosurgery, No. 1, vol. 64, Mar. 11-19, 2009.

Ebonia W. Elliott-Lewis et al., Evaluation of New Bipolar Coagulation Forceps in a Thermal Damage Assessment, Operative Neurosurgery, No. 6, vol. 65, 1182-1187, Dec. 2009.

Manuel Dujovny et al., Bipolar Coagulation in Neurosurgery, Surg. Neurol. 1998; 49:328-32.

Leonard I. Malis, Electrosurgery and Bipolar Technology, Operative Neurosurgery, No. 1, vol. 58, 1-12, Feb. 2006.

Ebonia W. Elliott-Lewis et al., Thermal Damage Assessment of Novel Bipolar Forceps in a Sheep Model of Spinal Surgery, Neurosurgery 67:166-172, 2010.

Soring Product Catalog, Sep. 2011.

510 (k) Summary of Safety and Effectiveness, K110924, Dec. 7, 2011.

* cited by examiner

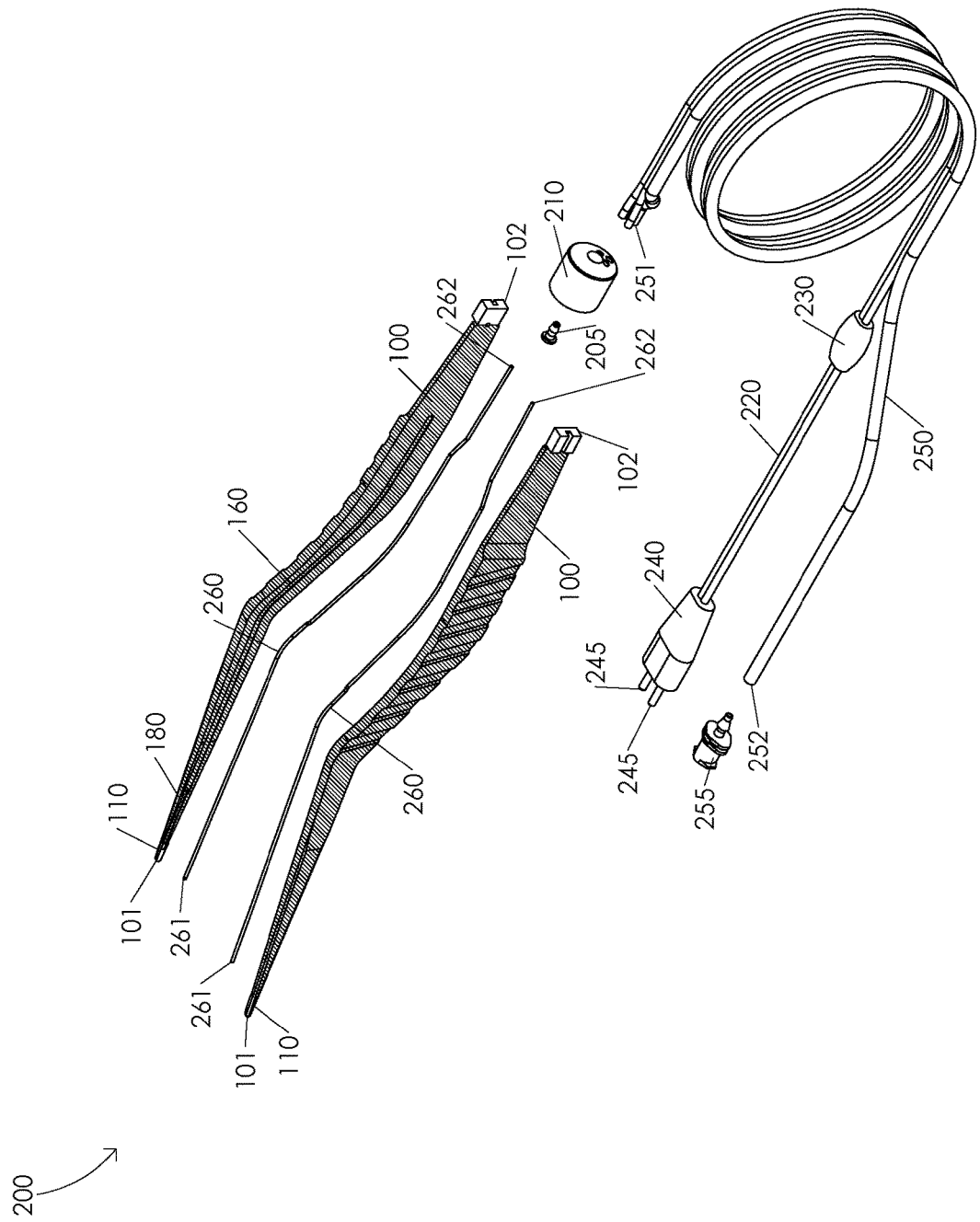

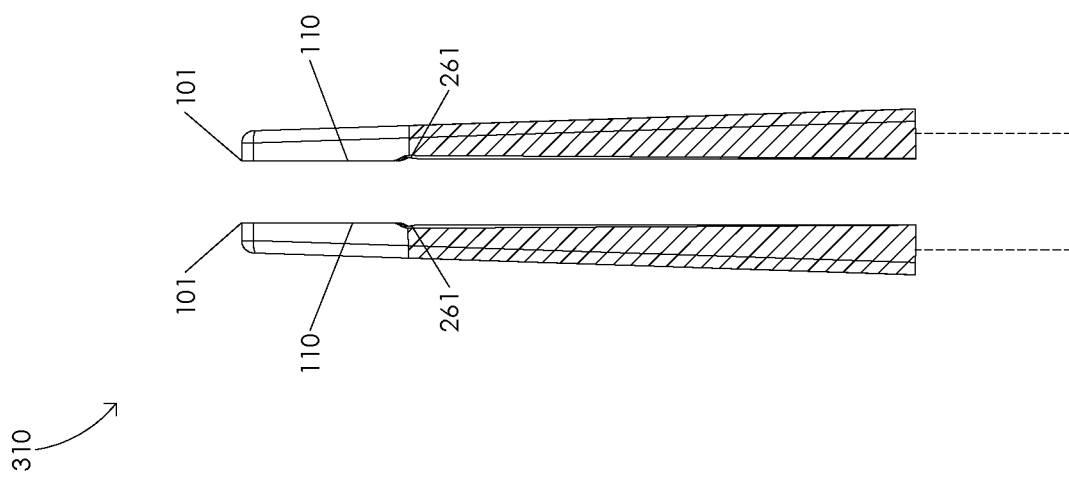
FIG. 3B
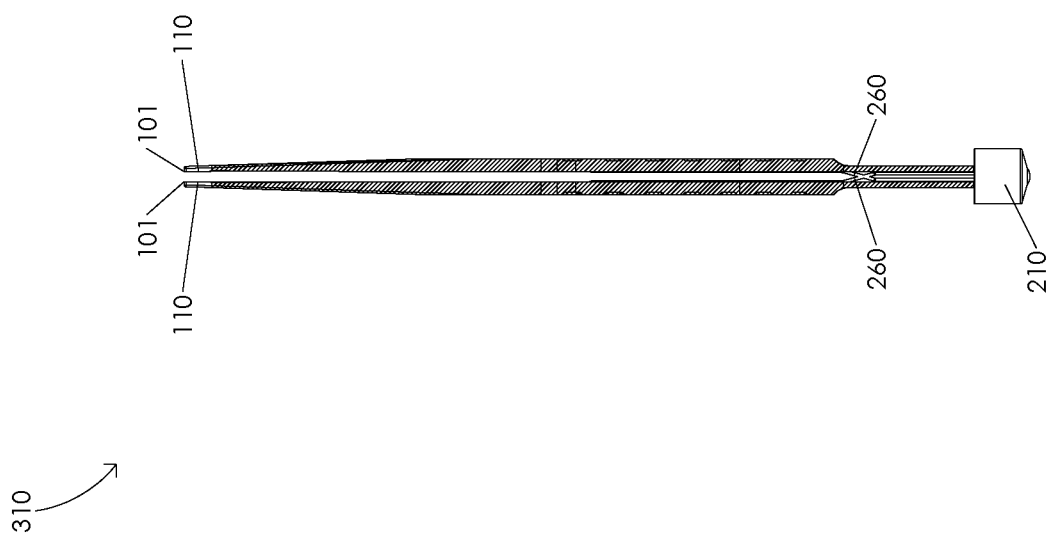

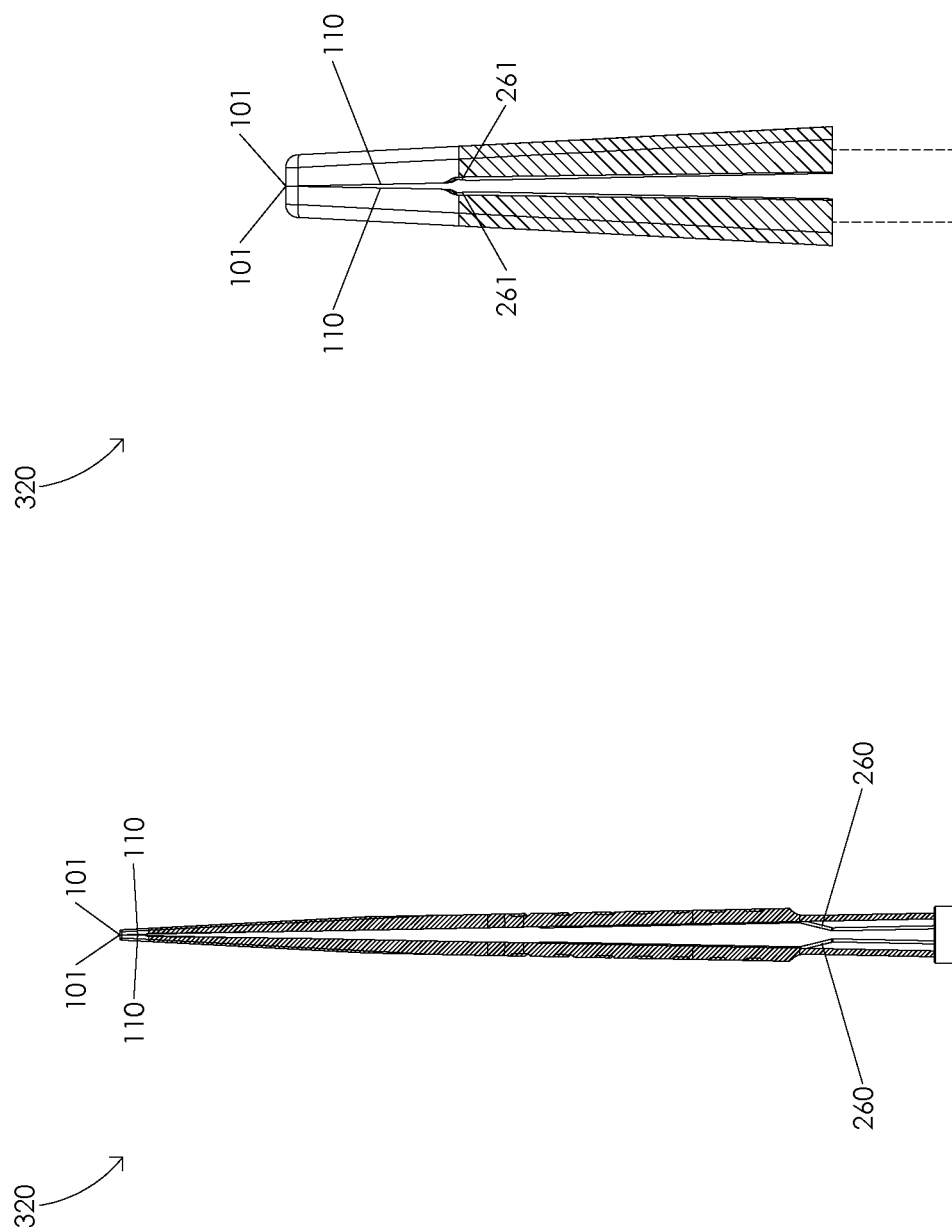

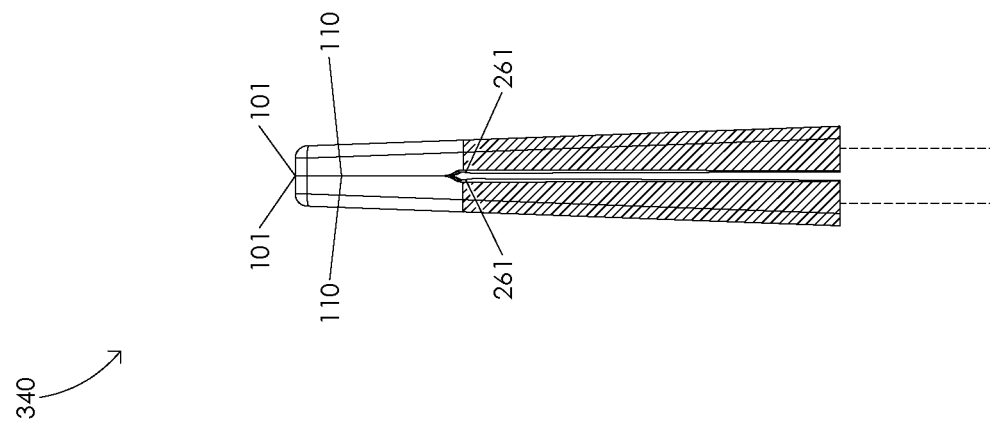
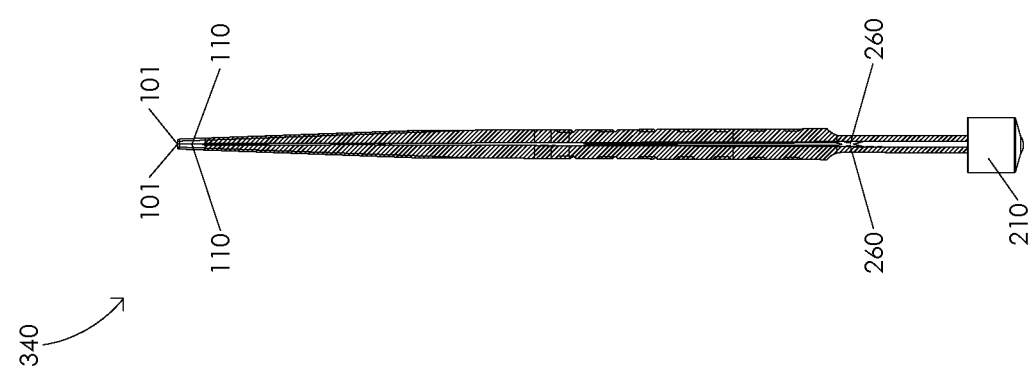
FIG. 3E

IRRIGATING BIPOLAR FORCEPS

CROSS-REFERENCE TO RELATED APPLICATIONS

This Application claims the benefit of U.S. Provisional Application No. 62/016,817, filed Jun. 25, 2014.

FIELD OF THE INVENTION

The present disclosure relates to a medical device, and, more particularly, to an electrosurgical instrument.

BACKGROUND OF THE INVENTION

A variety of complete surgical procedures and portions of surgical procedures may be performed with bipolar forceps, e.g., bipolar forceps are commonly used in dermatological, gynecological, cardiac, plastic, ocular, spinal, maxillofacial, orthopedic, urological, and general surgical procedures. Bipolar forceps are also used in neurosurgical procedures; however, the use of bipolar forceps in neurosurgical procedures presents unique risks to patients if the surgeon is unable to both visually and tactilely confirm that an electrosurgical procedure is being performed as intended. Moreover, a surgeon's view of a surgical site may become obstructed by debris, e.g., blood, tissue, etc. Accordingly, there is a need for a bipolar forceps that allows a surgeon to both visually and tactilely confirm that an electrosurgical procedure is being performed as intended and clear debris from a surgical site.

BRIEF SUMMARY OF THE INVENTION

The present disclosure presents an irrigating bipolar forceps. Illustratively, an irrigating bipolar forceps may comprise a first forceps arm, a conductor tip of the first forceps arm, a second forceps arm, a conductor tip of the second forceps arm, an input conductor isolation mechanism, and irrigation tubing. In one or more embodiments, a proximal end of the first forceps arm may be disposed within the input conductor isolation mechanism and a proximal end of the second forceps arm may be disposed within the input conductor isolation mechanism. Illustratively, an application of a force to a lateral portion of the forceps arms may be configured to close the forceps arms. In one or more embodiments, a reduction of a force applied to a lateral portion of the forceps arms may be configured to open the forceps arms. Illustratively, the irrigation tubing may be configured to transport a fluid from an irrigation supply system to a surgical site.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIG. 2 is a schematic diagram illustrating an exploded view of an irrigating bipolar forceps assembly;

FIGS. 3A, 3B, 3C, 3D, and 3E are schematic diagrams illustrating a gradual closing of an irrigating bipolar forceps;

DETAILED DESCRIPTION OF AN ILLUSTRATIVE EMBODIMENT

Figure 1A:
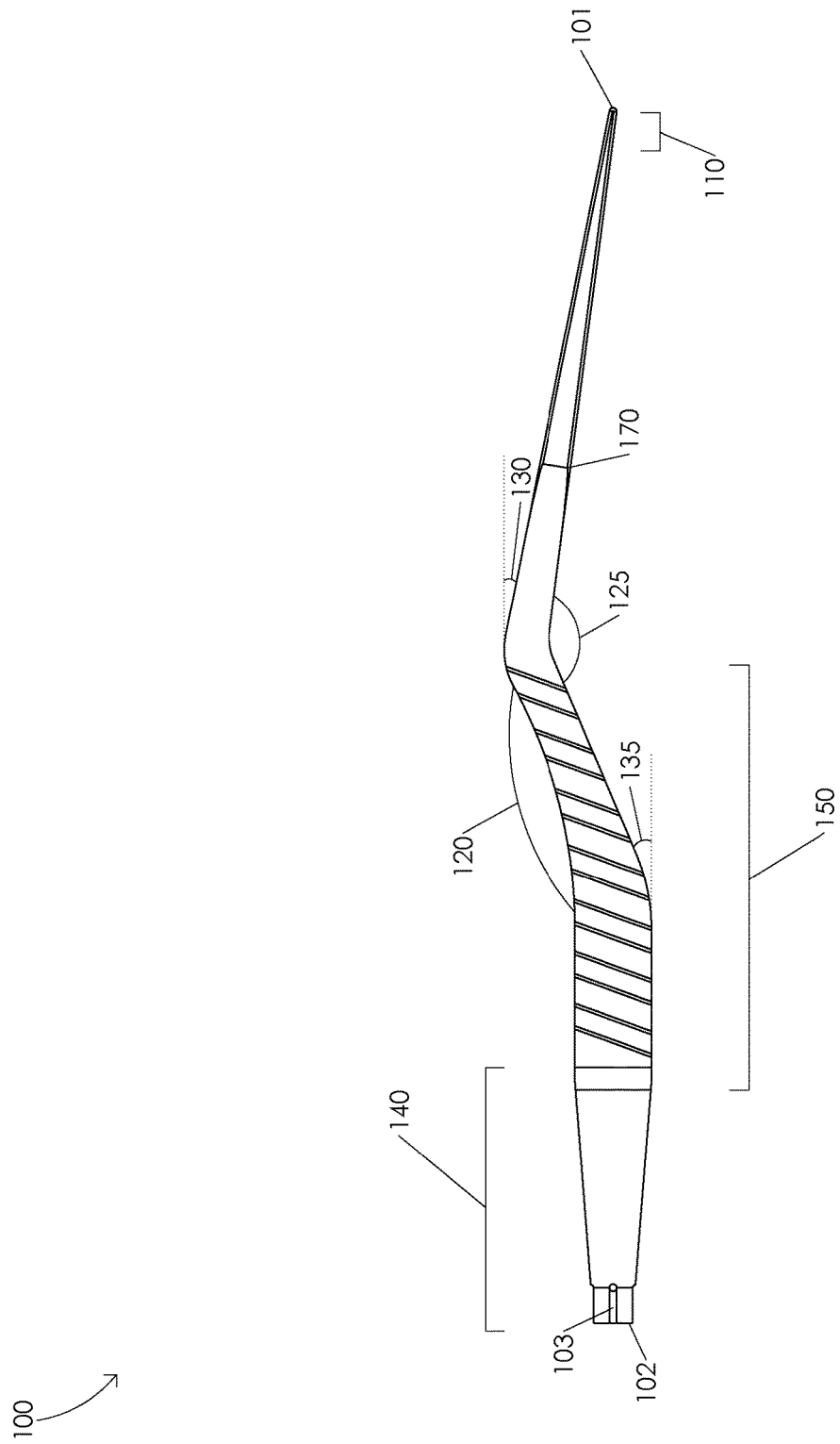
FIGS. 1A and 1B are schematic diagrams illustrating a forceps arm.
Figure 1B:
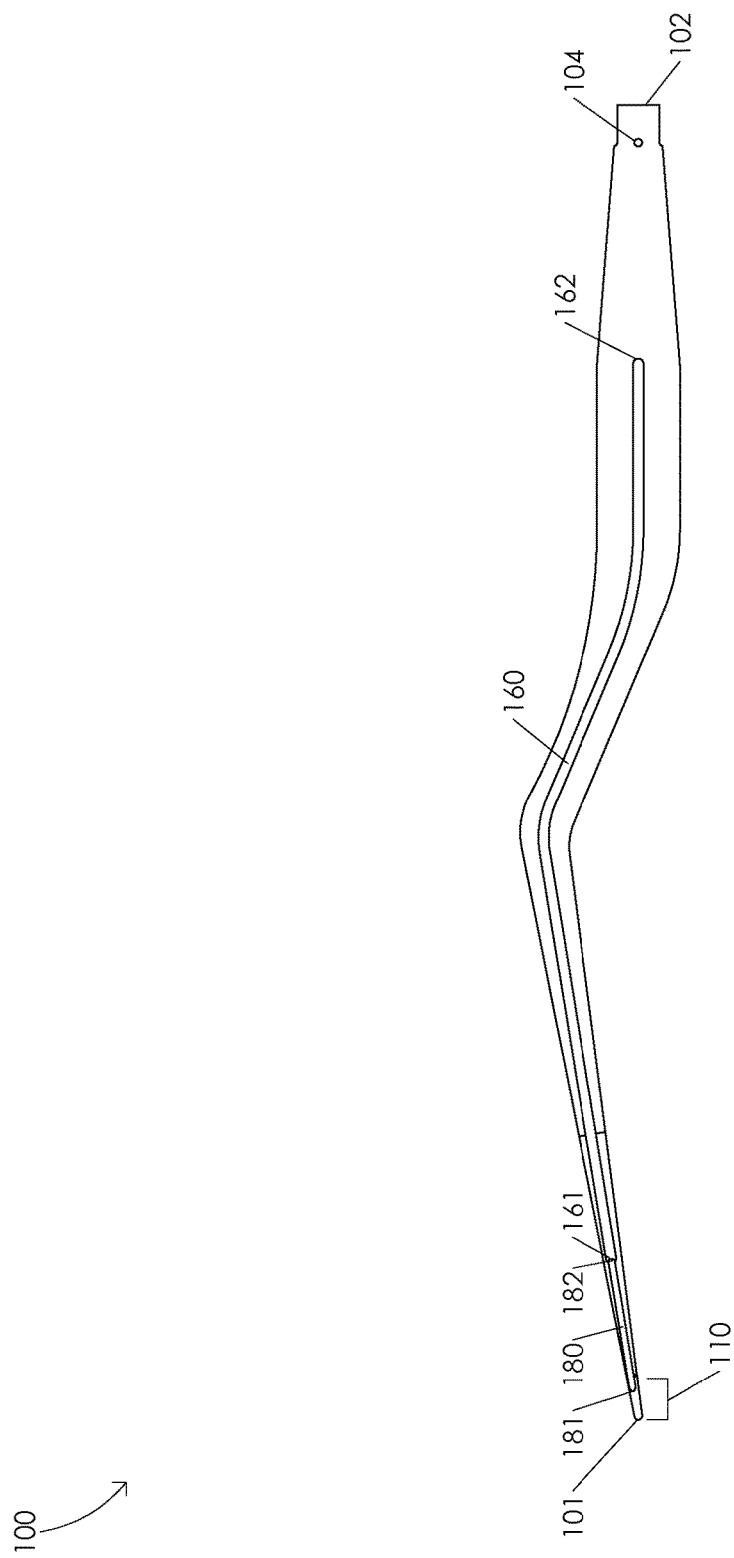

FIGS. 1A and 1B are schematic diagrams illustrating a forceps arm 100. FIG. 1A is a schematic diagram illustrating a lateral view of a forceps arm 100. Illustratively, a forceps arm 100 may comprise an input conductor housing 103, a conductor tip 110, a forceps arm superior incline angle 120, a forceps arm inferior decline angle 125, a forceps arm superior decline angle 130, a forceps arm inferior incline angle 135, a socket interface 140, a forceps arm grip 150, and a forceps jaw taper interface 170. FIG. 1B is a schematic diagram illustrating a medial view of a forceps arm 100. Illustratively, a forceps arm 100 may comprise a proximal channel 160 having a proximal channel distal end 161 and a proximal channel proximal end 162 and a distal channel 180 having a distal channel distal end 181 and a distal channel proximal end 182. In one or more embodiments, forceps arm 100 may be may be manufactured from any suitable material, e.g., polymers, metals, metal alloys, etc., or from any combination of suitable materials. Illustratively, forceps arm 100 may be manufactured from an electrically conductive material, e.g., metal, graphite, conductive polymers, etc. In one or more embodiments, forceps arm 100 may be manufactured from an electrically conductive metal, e.g., silver, copper, gold, aluminum, etc. Illustratively, forceps arm 100 may be manufactured from an electrically conductive metal alloy, e.g., a silver alloy, a copper alloy, a gold alloy, an aluminum alloy, stainless steel, etc.

In one or more embodiments, forceps arm 100 may be manufactured from a material having an electrical conductivity in a range of $30.0 \times 10^6$ to $40.0 \times 10^6$ Siemens per meter at a temperature of 20.0° C., e.g., forceps arm 100 may be manufactured from a material having an electrical conductivity of $35.5 \times 10^6$ Siemens per meter at a temperature of 20.0° C. Illustratively, forceps arm 100 may be manufactured from a material having an electrical conductivity of less than $30.0 \times 10^6$ Siemens per meter or greater than $40.0 \times 10^6$ Siemens per meter at a temperature of 20.0° C. In one or more embodiments, forceps arm 100 may be manufactured from a material having a thermal conductivity in a range of 180.0 to 250.0 Watts per meter Kelvin at a temperature of 20.0° C., e.g., forceps arm 100 may be manufactured from a material having a thermal conductivity of 204.0 Watts per meter Kelvin at a temperature of 20.0° C. Illustratively, forceps arm 100 may be manufactured from a material having a thermal conductivity of less than 180.0 Watts per meter Kelvin or greater than 250.0 Watts per meter Kelvin at a temperature of 20.0° C. In one or more embodiments, forceps arm 100 may be manufactured from a material having an electrical conductivity in a range of $30.0 \times 10^6$ to $40.0 \times 10^6$ Siemens per meter and a thermal conductivity in a range of 180.0 to 250.0 Watts per meter Kelvin at a temperature of 20.0° C., e.g., forceps arm 100 may be manufactured from a material having an electrical conductivity of $35.5 \times 10^6$ Siemens per meter and a thermal conductivity of 204.0 Watts per meter Kelvin at a temperature of 20.0° C.

Illustratively, forceps arm 100 may have a density in a range of 0.025 to 0.045 pounds per cubic inch, e.g., forceps arm 100 may have a density of 0.036 pounds per cubic inch. In one or more embodiments, forceps arm 100 may have a density less than 0.025 pounds per cubic inch or greater than 0.045 pounds per cubic inch. For example, forceps arm 100 may have a density of 0.0975 pounds per cubic inch. Illustratively, forceps arm 100 may have a mass in a range of 0.0070 to 0.0092 pounds, e.g., forceps arm 100 may have a mass of 0.0082 pounds. In one or more embodiments, forceps arm 100 may have a mass less than 0.0070 pounds or greater than 0.0092 pounds. Illustratively, forceps arm 100 may have a volume in a range of 0.20 to 0.26 cubic inches, e.g., forceps arm 100 may have a volume of 0.227 cubic inches. In one or more embodiments, forceps arm 100 may have a volume less than 0.20 cubic inches or greater than 0.26 cubic inches. Illustratively, forceps arm 100 may have a surface area in a range of 5.0 to 8.0 square inches, e.g., forceps arm 100 may have a surface area of 6.9 square inches. In one or more embodiments, forceps arm 100 may have a surface area less than 5.0 square inches or greater than 8.0 square inches. Illustratively, conductor tip 110 may have a surface area in a range of 0.03 to 0.07 square inches, e.g., conductor tip 110 may have a surface area of 0.053 square inches. In one or more embodiments, conductor tip 110 may have a surface area less than 0.03 square inches or greater than 0.07 square inches. Illustratively, a ratio of forceps arm 100 surface area to conductor tip 110 surface area may be in a range of 100.0 to 180.0, e.g., a ratio of forceps arm 100 surface area to conductor tip 110 surface area may be 137.9. In one or more embodiments, a ratio of forceps arm 100 surface area to conductor tip 110 surface area may be less than 100.0 or greater than 180.0.

Illustratively, conductor tip 110 may be configured to prevent tissue from sticking to conductor tip 110. In one or more embodiments, conductor tip 110 may comprise an evenly polished material configured to prevent tissue sticking. In one or more embodiments, a surface of conductor tip 110 may have a roughness average in a range of 25.0 to 150.0 nanometers, e.g., a surface of conductor tip 110 may have a roughness average of 98.8 nanometers. Illustratively, a surface of conductor tip 110 may have a roughness average of less than 25.0 nanometers or greater than 150.0 nanometers. In one or more embodiments, a surface of conductor tip 110 may have a root mean square average between height deviations over a total surface area of conductor tip 110 in a range of 30.0 to 150.0 nanometers, e.g., a surface of conductor tip 110 may have a root mean square average between height deviations over a total surface area of conductor tip 110 of 112.0 nanometers. Illustratively, a surface of conductor tip 110 may have a root mean square average between height deviations over a total surface area of conductor tip 110 of less than 30.0 nanometers or greater than 150.0 nanometers. In one or more embodiments, a surface of conductor tip 110 may have an average maximum profile of the ten greatest peak-to-valley separations over a total surface area of conductor tip 110 in a range of 100.0 to 850.0 nanometers, e.g., a surface of conductor tip 110 may have an average maximum profile of the ten greatest peak-to-valley separations over a total surface area of conductor tip 110 of 435.0 nanometers. Illustratively, a surface of conductor tip 110 may have an average maximum profile of the ten greatest peak-to-valley separations over a total surface area of conductor tip 110 of less than 100.0 nanometers or greater than 850.0 nanometers. In one or more embodiments, a surface of conductor tip 110 may have a maximum height difference between a highest point and a lowest point of a total surface area of conductor tip 110 in a range of 200.0 to 1300.0 nanometers, e.g., a surface of conductor tip 110 may have a maximum height difference between a highest point and a lowest point of a total surface area of conductor tip 110 of 650.0 nanometers. Illustratively, a surface of conductor tip 110 may have a maximum height difference between a highest point and a lowest point of a total surface area of conductor tip 110 of less than 200.0 nanometers or greater than 1300.0 nanometers.

Illustratively, conductor tip 110 may have a length in a range of 0.22 to 0.3 inches, e.g., conductor tip 110 may have a length of 0.26 inches. In one or more embodiments, conductor tip 110 may have a length less than 0.22 inches or greater than 0.3 inches. Illustratively, conductor tip 110 may have a width in a range of 0.018 to 0.062 inches, e.g., conductor tip 110 may have a width of 0.04 inches. In one or more embodiments, conductor tip 110 may have a width less than 0.018 inches or greater than 0.062 inches. Illustratively, a geometry of forceps arm 100 may comprise a tapered portion, e.g., a tapered portion from forceps jaw taper interface 170 to forceps arm distal end 101. In one or more embodiments, forceps arm 100 may comprise a tapered portion having a tapered angle in a range of 3.0 to 4.5 degrees, e.g., forceps arm 100 may comprise a tapered portion having a tapered angle of 3.72 degrees. Illustratively, forceps arm 100 may comprise a tapered portion having a tapered angle of less than 3.0 degrees or greater than 4.5 degrees.

In one or more embodiments, proximal channel 160 may have a diameter in a range of 1.25 to 1.75 millimeters, e.g., proximal channel 160 may have a diameter of 1.5875 millimeters. Illustratively, proximal channel 160 may have a diameter of less than 1.25 millimeters or greater than 1.75 millimeters. In one or more embodiments, proximal channel 160 may have a depth in a range of 0.035 to 0.040 inches, e.g., proximal channel 160 may have a depth of 0.038 inches. Illustratively, proximal channel 160 may have a depth of less than 0.035 inches or greater than 0.040 inches. In one or more embodiments, proximal channel 160 may have a surface area in a range of 0.5 to 0.8 square inches, e.g., proximal channel 160 may have a surface area of 0.636 square inches. Illustratively, proximal channel 160 may have a surface area of less than 0.5 square inches or greater than 0.8 square inches. In one or more embodiments, proximal channel 160 may have a volume in a range of 0.015 to 0.025 cubic inches, e.g., proximal channel 160 may have a volume of 0.01995 cubic inches. Illustratively, proximal channel 160 may have a volume of less than 0.015 cubic inches or greater than 0.025 cubic inches.

In one or more embodiments, distal channel 180 may have a diameter in a range of 0.75 to 1.25 millimeters, e.g., distal channel 180 may have a diameter of 1.0 millimeters. Illustratively, distal channel 180 may have a diameter of less than 0.75 millimeters or greater than 1.25 millimeters. In one or more embodiments, distal channel 180 may have a depth in a range of 0.035 to 0.040 inches, e.g., distal channel 180 may have a depth of 0.038 inches. Illustratively, distal channel 180 may have a depth of less than 0.035 inches or greater than 0.040 inches. In one or more embodiments, distal channel 180 may have a surface area in a range of 0.04 to 0.08 square inches, e.g., distal channel 180 may have a surface area of 0.066 square inches. Illustratively, distal channel 180 may have a surface area of less than 0.04 square inches or greater than 0.08 square inches. In one or more embodiments, distal channel 180 may have a volume in a range of 0.0005 to 0.0015 cubic inches, e.g., distal channel 180 may have a volume of 0.001 cubic inches. Illustratively, distal channel 180 may have a volume of less than 0.0005 cubic inches or greater than 0.0015 cubic inches. In one or more embodiments, a portion of distal channel 180 may extend a distance into conductor tip 110, e.g., distal channel distal end 181 may be disposed within conductor tip 110. Illustratively, a portion of distal channel 180 may extend a distance in a range of 0.001 to 0.135 inches into conductor tip 110, e.g., distal channel distal end 181 may extend a distance of 0.1 inches into conductor tip 110. In one or more embodiments, a portion of distal channel 180 may extend into conductor tip 110 a distance of less than 0.001 inches or greater than 0.135 inches. Illustratively, a portion of distal channel 180 extending into conductor tip 110 may have a surface area in a range of 0.001 to 0.005 square inches, e.g., a portion of distal channel 180 extending into conductor tip 110 may have a surface area of 0.0033 square inches. In one or more embodiments, a portion of distal channel 180 extending into conductor tip 110 may have a surface area of less than 0.001 square inches or greater than 0.005 square inches.

Illustratively, forceps arm 100 may comprise a material having a modulus of elasticity in a range of $9.0 \times 10^6$ to $11.0 \times 10^6$ pounds per square inch, e.g., forceps arm 100 may comprise a material having a modulus of elasticity of $10.0 \times 10^6$ pounds per square inch. In one or more embodiments, forceps arm 100 may comprise a material having a modulus of elasticity less than $9.0 \times 10^6$ pounds per square inch or greater than $11.0 \times 10^6$ pounds per square inch. Illustratively, forceps arm 100 may comprise a material having a shear modulus in a range of $3.5 \times 10^6$ to $4.5 \times 10^6$ pounds per square inch, e.g., forceps arm 100 may comprise a material having a shear modulus of $3.77 \times 10^6$ pounds per square inch. In one or more embodiments, forceps arm 100 may comprise a material having a shear modulus less than $3.5 \times 10^6$ pounds per square inch or greater than $4.5 \times 10^6$ pounds per square inch.

Illustratively, forceps arm superior incline angle 120 may comprise any angle greater than 90.0 degrees. In one or more embodiments, forceps arm superior incline angle 120 may comprise any angle in a range of 150.0 to 170.0 degrees, e.g., forceps arm superior incline angle 120 may comprise a 160.31 degree angle. Illustratively, forceps arm superior incline angle 120 may comprise an angle less than 150.0 degrees or greater than 170.0 degrees. In one or more embodiments, forceps arm inferior decline angle 125 may comprise any angle greater than 90.0 degrees. Illustratively, forceps arm inferior decline angle 125 may comprise any angle in a range of 140.0 to 160.0 degrees, e.g., forceps arm inferior decline angle 125 may comprise a 149.56 degree angle. In one or more embodiments, forceps arm inferior decline angle 125 may comprise an angle less than 140.0 degrees or greater than 160.0 degrees. Illustratively, forceps arm inferior decline angle 125 may comprise any angle less than forceps arm superior incline angle 120, e.g., forceps arm inferior decline angle 125 may comprise an angle in a range of 5.0 to 15.0 degrees less than forceps arm superior incline angle 120. In one or more embodiments, forceps arm inferior decline angle 125 may comprise an angle less than 5.0 degrees or greater than 15.0 degrees less than forceps arm superior incline angle 120.

Illustratively, forceps arm superior decline angle 130 may comprise any angle less than 90.0 degrees. In one or more embodiments, forceps arm superior decline angle 130 may comprise any angle in a range of 5.0 to 15.0 degrees, e.g., forceps arm superior decline angle 130 may comprise an 11.3 degree angle. Illustratively, forceps arm superior decline angle 130 may comprise an angle less than 5.0 degrees or greater than 15.0 degrees. In one or more embodiments, forceps arm inferior incline angle 135 may comprise any angle less than 90.0 degrees. Illustratively, forceps arm inferior incline angle 135 may comprise any angle in a range of 15.0 to 30.0 degrees, e.g., forceps arm inferior incline angle 135 may comprise a 23.08 degree angle. In one or more embodiments, forceps arm inferior incline angle 135 may comprise an angle less than 15.0 degrees or greater than 30.0 degrees. Illustratively, forceps arm inferior incline angle 135 may comprise any angle greater than forceps arm superior decline angle 130, e.g., forceps arm inferior incline angle 135 may comprise an angle in a range of 5.0 to 15.0 degrees greater than forceps arm superior decline angle 130. In one or more embodiments, forceps arm inferior incline angle 135 may comprise an angle less than 5.0 degrees or greater than 15.0 degrees greater than forceps arm superior decline angle 130.

FIG. 2 is a schematic diagram illustrating an exploded view of an irrigating bipolar forceps assembly 200. In one or more embodiments, an irrigating bipolar forceps assembly 200 may comprise a pair of forceps arms 100, an irrigation fluid multiplexer 205, an input conductor isolation mechanism 210, a bipolar cord 220, a bipolar cord separation control 230, an electrosurgical generator adapter 240, an electrosurgical generator interface 245, irrigation tubing 250, an irrigation supply adapter 255, and a fluid transport tube 260. Illustratively, a portion of each forceps arm 100 may be coated with a material having a high electrical resistivity, e.g., a portion of each forceps arm 100 may be coated with an electrical insulator material. In one or more embodiments, input conductor housings 103 and conductor tips 110 may not be coated with a material, e.g., input conductor housings 103 and conductor tips 110 may comprise electrical leads. Illustratively, a portion of each forceps arm 100 may be coated with a thermoplastic material, e.g., a portion of each forceps arm 100 may be coated with nylon. In one or more embodiments, a portion of each forceps arm 100 may be coated with a fluoropolymer, e.g., a portion of each forceps arm 100 may be coated with polyvinylidene fluoride. Illustratively, a portion of each forceps arm 100 may be coated with a material having an electrical conductivity less than $1.0 \times 10^{-8}$ Siemens per meter at a temperature of 20.0° C., e.g., a portion of each forceps arm 100 may be coated with a material having an electrical conductivity of $1.0 \times 10^{-12}$ Siemens per meter at a temperature of 20.0° C. In one or more embodiments, a portion of each forceps arm 100 may be coated with a material having a thermal conductivity of less than 1.0 Watts per meter Kelvin at a temperature of 20.0° C., e.g., a portion of each forceps arm 100 may be coated with a material having a thermal conductivity of 0.25 Watts per meter Kelvin at a temperature of 20.0° C. Illustratively, a portion of each forceps arm 100 may be coated with a material having an electrical conductivity of less than $1.0 \times 10^{-8}$ Siemens per meter and a thermal conductivity of less than 1.0 Watts per meter Kelvin at a temperature of 20.0° C., e.g., a portion of each forceps arm 100 may be coated with a material having an electrical conductivity of $1.0 \times 10^{-12}$ Siemens per meter and a thermal conductivity of 0.25 Watts per meter Kelvin at a temperature of 20.0° C. In one or more embodiments, a portion of each forceps arm 100 may be coated with a material wherein a coating thickness of the material is in a range of 0.005 to 0.008 inches, e.g., a portion of each forceps arm 100 may be coated with a material wherein a coating thickness of the material is 0.0065 inches. Illustratively, a portion of each forceps arm 100 may be coated with a material wherein a coating thickness of the material is less than 0.005 inches or greater than 0.008 inches. In one or more embodiments, a portion of each forceps arm 100 may be coated with a material having an electrical conductivity of less than $1.0 \times 10^{-8}$ Siemens per meter and a thermal conductivity of less than 1.0 Watts per meter Kelvin at a temperature of 20.0° C. wherein a coating thickness of the material is in a range of 0.005 to 0.008 inches, e.g., a portion of each forceps arm 100 may be coated with a material having an electrical conductivity of $1.0 \times 10^{-12}$ Siemens per meter and a thermal conductivity of 0.25 Watts per meter Kelvin at a temperature of 20.0° C. wherein a coating thickness of the material is 0.0065 inches. Illustratively, a portion of each forceps arm 100 may be coated with a material having a material mass in a range of 0.0015 to 0.0025 pounds, e.g., a portion of each forceps arm 100 may be coated with a material having a material mass of 0.0021 pounds. In one or more embodiments, a portion of each forceps arm 100 may be coated with a material having a material mass less than 0.0015 pounds or greater than 0.0025 pounds.

Illustratively, input conductor isolation mechanism 210 may comprise a first forceps arm housing and a second forceps arm housing. In one or more embodiments, input conductor isolation mechanism 210 may be configured to separate a first bipolar input conductor and a second bipolar input conductor, e.g., input conductor isolation mechanism 210 comprise a material with an electrical resistivity greater than $1 \times 10^{16}$ ohm meters. Illustratively, input conductor isolation mechanism 210 may comprise a material with an electrical resistivity less than or equal to $1 \times 10^{16}$ ohm meters. In one or more embodiments, input conductor isolation mechanism 210 may comprise an interface between bipolar cord 220 and forceps arms 100. Illustratively, a first bipolar input conductor and a second bipolar input conductor may be disposed within bipolar cord 220, e.g., bipolar cord 220 may be configured to separate the first bipolar input conductor and the second bipolar input conductor. In one or more embodiments, a first bipolar input conductor may be electrically connected to first forceps arm 100, e.g., the first bipolar input conductor may be disposed within input conductor housing 103. Illustratively, a second bipolar input conductor may be electrically connected to second forceps arm 100, e.g., the second bipolar input conductor may be disposed within input conductor housing 103. In one or more embodiments, a portion of first forceps arm 100 may be disposed within a first forceps arm housing, e.g., first forceps arm proximal end 102 may be disposed within a first forceps arm housing. Illustratively, first forceps arm 100 may be fixed within a first forceps arm housing, e.g., by an adhesive or any suitable fixation means. In one or more embodiments, a first bipolar input conductor may be disposed within a first forceps arm housing, e.g., the first bipolar input conductor may be electrically connected to first forceps arm 100. Illustratively, a first bipolar input conductor may be fixed within a first forceps arm housing wherein the first bipolar input conductor is electrically connected to first forceps arm 100. In one or more embodiments, a portion of second forceps arm 100 may be disposed within a second forceps arm housing, e.g., second forceps arm proximal end 102 may be disposed within a second forceps arm housing. Illustratively, second forceps arm 100 may be fixed within a second forceps arm housing, e.g., by an adhesive or any suitable fixation means. In one or more embodiments, a second bipolar input conductor may be disposed within a second forceps arm housing, e.g., the second bipolar input conductor may be electrically connected to second forceps arm 100. Illustratively, a second bipolar input conductor may be fixed within a second forceps arm housing wherein the second bipolar input conductor is electrically connected to second forceps arm 100.

In one or more embodiments, electrosurgical generator adaptor 240 may comprise a first electrosurgical generator interface 245 and a second electrosurgical generator interface 245. Illustratively, first electrosurgical generator interface 245 and second electrosurgical generator interface 245 may be configured to connect to an electrosurgical generator. In one or more embodiments, connecting first electrosurgical generator interface 245 and second electrosurgical generator interface 245 to an electrosurgical generator may be configured to electrically connect a first bipolar input conductor to a first electrosurgical generator output and to electrically connect a second bipolar input conductor to a second electrosurgical generator output. Illustratively, connecting a first bipolar input conductor to a first electrosurgical generator output may be configured to electrically connect first forceps arm 100 to the first electrosurgical generator output. In one or more embodiments, connecting a second bipolar input conductor to a second electrosurgical generator output may be configured to electrically connect second forceps arm 100 to the second electrosurgical generator output.

Illustratively, irrigation tubing 250 may comprise an irrigation tubing distal end 251 and an irrigation tubing proximal end 252. In one or more embodiments, irrigation tubing 250 may be configured to contain an irrigation fluid, e.g., saline. Illustratively, a portion of irrigation supply adaptor 255 may be disposed within a portion of irrigation tubing 250, e.g., a portion of irrigation supply adaptor 255 may be disposed within irrigation tubing proximal end 252. In one or more embodiments, irrigation supply adaptor 255 may comprise a female luer connector. Illustratively, a portion of irrigation supply adaptor 255 may be fixed within a portion of irrigation tubing 250, e.g., a portion of irrigation supply adaptor 255 may be fixed within irrigation tubing proximal end 252 by a friction fit, an adhesive, or any suitable fixation means. In one or more embodiments, irrigation supply adaptor 255 may be configured to interface with an irrigation supply system, e.g., irrigation supply adaptor 255 may be configured to interface with a pressurized irrigation source. Illustratively, irrigation supply adaptor 255 may be configured to interface with an irrigation supply system having a peristaltic pump. In one or more embodiments, irrigation supply adaptor 255 may be configured to interface with a gravity infusion irrigation source, a single roller irrigation source, a double roller pump irrigation source, etc. In one or more embodiments, a portion of irrigation tubing 250 may be disposed within input conductor isolation mechanism 210, e.g., irrigation tubing distal end 251 may be disposed within input conductor isolation mechanism 210. Illustratively, a portion of irrigation tubing 250 may be fixed within input conductor isolation mechanism 210, e.g., a portion of irrigation tubing 250 may be fixed within input conductor isolation mechanism 210 by an adhesive or any suitable fixation means.

In one or more embodiments, a portion of irrigation fluid multiplexer 205 may be disposed within irrigation tubing 250, e.g., a portion of irrigation fluid multiplexer 205 may be disposed within irrigation tubing distal end 251. Illustratively, a portion of irrigation fluid multiplexer 205 may be fixed within irrigation tubing 250, e.g., a portion of irrigation fluid multiplexer 205 may be fixed within irrigation tubing 250 by a friction fit, an adhesive, or any suitable fixation means. In one or more embodiments, a portion of irrigation fluid multiplexer 205 may be disposed within input conductor isolation mechanism 210. Illustratively, a portion of irrigation fluid multiplexer 205 may be fixed within input conductor isolation mechanism 210, e.g., a portion of irrigation fluid multiplexer 205 may be fixed within input conductor isolation mechanism 210 by an adhesive or any suitable fixation means.

In one or more embodiments, irrigation fluid multiplexer 205 may be configured to control a flow of irrigation fluid, e.g., irrigation fluid multiplexer 205 may be configured to direct a flow of irrigation fluid into a fluid transport tube 260. Illustratively, irrigation fluid multiplexer 205 may be configured to direct irrigation fluid out from irrigation tubing 250 and into a fluid transport tube 260. In one or more embodiments, irrigation fluid multiplexer 205 may selectively control a flow of irrigation fluid, e.g., irrigation fluid multiplexer 205 may direct a first amount of irrigation fluid into a first fluid transport tube 260 and irrigation fluid multiplexer 205 may direct a second amount of irrigation fluid into a second fluid transport tube 260. Illustratively, irrigation fluid multiplexer 205 may determine an amount of irrigation fluid to direct into a particular fluid transport tube 260 based on one or more events, e.g., irrigation fluid multiplexer 205 may be configured to increase an amount of irrigation fluid directed into a particular fluid transport tube 260 in response to an increase in a temperature of a particular conductor tip 110. In one or more embodiments, irrigation fluid multiplexer 205 may be configured to restrict an amount of irrigation fluid flowing into a fluid transport tube 260, e.g., irrigation fluid multiplexer 205 may be configured to prevent fluid transport tube 260 from experiencing unintended increases in fluid pressure.

In one or more embodiments, fluid transport tube 260 may be may be manufactured from any suitable material, e.g., polymers, metals, metal alloys, etc., or from any combination of suitable materials. For example, fluid transport tube 260 may be manufactured from polyimide. Illustratively, fluid transport tube 260 may be manufactured from a material configured to function at a temperature in a range of 0.0 to 400.0 degrees Celsius. In one or more embodiments, fluid transport tube 260 may be manufactured from a material having a thermal conductivity in a range of 0.4 to 0.5 Watts per meter Kelvin, e.g., fluid transport tube 260 may be manufactured from a material having a thermal conductivity of 0.471 Watts per meter Kelvin. Illustratively, fluid transport tube 260 may be manufactured from a material having a thermal conductivity of less than 0.4 Watts per meter Kelvin or greater than 0.5 Watts per meter Kelvin. In one or more embodiments, fluid transport tube 260 may be manufactured from a material having a tensile strength in a range of 25.0 to 35.0 kpsi, e.g., fluid transport tube 260 may be manufactured from a material having a tensile strength of 30.0 kpsi. Illustratively, fluid transport tube 260 may be manufactured from a material having a tensile strength of less than 25.0 kpsi or greater than 35.0 kpsi. In one or more embodiments, fluid transport tube 260 may be manufactured from a material having a modulus of elasticity in a range of 300.0 to 330.0 kpsi, e.g., fluid transport tube 260 may be manufactured from a material having a modulus of elasticity of 310.0 kpsi. Illustratively, fluid transport tube 260 may be manufactured from a material having a modulus of elasticity of less than 300.0 kpsi or greater than 330.0 kpsi. In one or more embodiments, fluid transport tube 260 may have an inner diameter in a range of 0.024 to 0.03 inches, e.g., fluid transport tube 260 may have an inner diameter of 0.027 inches. Illustratively, fluid transport tube 260 may have an inner diameter of less than 0.024 inches or greater than 0.03 inches. In one or more embodiments, fluid transport tube 260 may have an outer diameter in a range of 0.025 to 0.032 inches, e.g., fluid transport tube 260 may have an outer diameter of 0.029 inches. Illustratively, fluid transport tube 260 may have an outer diameter of less than 0.025 inches or greater than 0.032 inches.

Illustratively, irrigating bipolar forceps assembly 200 may comprise a first fluid transport tube 260, a first forceps arm 100, a second fluid transport tube 260, and a second forceps arm 100. In one or more embodiments, a portion of a first fluid transport tube 260 may be disposed within irrigation fluid multiplexer 205, e.g., a first fluid transport tube proximal end 262 may be disposed within irrigation fluid multiplexer 205. Illustratively, first fluid transport tube 260 may be disposed within a portion of first forceps arm 100, e.g., first fluid transport tube 260 may be disposed in proximal channel 160. In one or more embodiments, first fluid transport tube 260 may be disposed in distal channel 180, e.g., first fluid transport tube 260 may be disposed within distal channel 180 wherein a first fluid transport tubing distal end 261 is adjacent to distal channel distal end 181. Illustratively, a portion of first fluid transport tube 260 may be fixed within a portion of first forceps arm 100, e.g., a portion of first fluid transport tube 260 may be fixed within proximal channel 160. In one or more embodiments, a portion of first fluid transport tube 260 may be fixed within proximal channel 160 by a friction fit, an adhesive, or any suitable fixation means. Illustratively, one or more dimensions of proximal channel 160 and one or more dimensions of first fluid transport tube 260 may be configured to retain first fluid transport tube 260 within proximal channel 160, e.g., first fluid transport tube distal end 261 may be guided into proximal channel proximal end 162. In one or more embodiments, a portion of a second fluid transport tube 260 may be disposed within irrigation fluid multiplexer 205, e.g., a second fluid transport tube proximal end 262 may be disposed within irrigation fluid multiplexer 205. Illustratively, second fluid transport tube 260 may be disposed within a portion of second forceps arm 100, e.g., second fluid transport tube 260 may be disposed in proximal channel 160. In one or more embodiments, second fluid transport tube 260 may be disposed in distal channel 180, e.g., second fluid transport tube 260 may be disposed within distal channel 180 wherein a second fluid transport tubing distal end 261 is adjacent to distal channel distal end 181. Illustratively, a portion of second fluid transport tube 260 may be fixed within a portion of second forceps arm 100, e.g., a portion of second fluid transport tube 260 may be fixed within proximal channel 160. In one or more embodiments, a portion of second fluid transport tube 260 may be fixed within proximal channel 160 by a friction fit, an adhesive, or any suitable fixation means. Illustratively, one or more dimensions of proximal channel 160 and one or more dimensions of second fluid transport tube 260 may be configured to retain second fluid transport tube 260 within proximal channel 160, e.g., first fluid transport tube distal end 261 may be guided into proximal channel proximal end 162.

Illustratively, an irrigation fluid may ingress irrigation tubing 250 at irrigation tubing proximal end 252. The irrigation fluid may flow though irrigation tubing 250 and egress irrigation tubing 250 at irrigation tubing distal end 251. In one or more embodiments, irrigation fluid multiplexer 205 may be configured to direct the irrigation fluid into a first fluid transport tube 260. Illustratively, the irrigation fluid may ingress a first fluid transport tube 260 at a first fluid transport tube proximal end 262. The irrigation fluid may flow through first fluid transport tube 260 and egress first fluid transport tube 260 at first fluid transport tube distal end 261. In one or more embodiments, irrigation fluid egressing first fluid transport tube 260 may be configured to reduce a temperature of a first conductor tip 110. Illustratively, irrigation fluid egressing first fluid transport tube 260 may be configured to prevent tissue from sticking to a first conductor tip 110. In one or more embodiments, irrigation fluid egressing first fluid transport tube 260 may be configured to modify a physical property of first conductor tip 110 or a target tissue, e.g., irrigation fluid egressing first fluid transport tube 260 may be configured to increase an electrical conductance through first conductor tip 110 and the target tissue. In one or more embodiments, irrigation fluid multiplexer 205 may be configured to direct irrigation fluid into a second fluid transport tube 260. Illustratively, the irrigation fluid may ingress a second fluid transport tube 260 at a second fluid transport tube proximal end 262. The irrigation fluid may flow through second fluid transport tube 260 and egress second fluid transport tube 260 at second fluid transport tube distal end 261. In one or more embodiments, irrigation fluid egressing second fluid transport tube 260 may be configured to reduce a temperature of a second conductor tip 110. Illustratively, irrigation fluid egressing second fluid transport tube 260 may be configured to prevent tissue from sticking to a second conductor tip 110. In one or more embodiments, irrigation fluid egressing second fluid transport tube 260 may be configured to modify a physical property of second conductor tip 110 or a target tissue, e.g., irrigation fluid egressing second fluid transport tube 260 may be configured to increase an electrical conductance through second conductor tip 110 and the target tissue. In one or more embodiments, irrigation fluid multiplexer 205 may be configured to direct irrigation fluid into a first fluid transport tube 260 and into a second fluid transport tube 260. Illustratively, the irrigation fluid may ingress a first fluid transport tube 260 at a first fluid transport tube proximal end 262 and the irrigation fluid may ingress a second fluid transport tube 260 at a second fluid transport tube proximal end 262. The irrigation fluid may flow through first fluid transport tube 260 and egress first fluid transport tube 260 at first fluid transport tube distal end 261 and the irrigation fluid may flow through second fluid transport tube 260 and egress second fluid transport tube 260 at second fluid transport tube distal end 261. In one or more embodiments, irrigation fluid egressing first fluid transport tube 260 may be configured to reduce a temperature of a first conductor tip 110 and irrigation fluid egressing second fluid transport tube 260 may be configured to reduce a temperature of a second conductor tip 110. Illustratively, irrigation fluid egressing first fluid transport tube 260 may be configured to prevent tissue from sticking to a first conductor tip 110 and irrigation fluid egressing second fluid transport tube 260 may be configured to prevent tissue from sticking to a second conductor tip 110. In one or more embodiments, irrigation fluid egressing first fluid transport tube 260 and second fluid transport tube 260 may be configured to modify a physical property of first conductor tip 110 or second conductor tip 110 or a target tissue, e.g., irrigation fluid egressing first fluid transport tube 260 and second fluid transport tube 260 may be configured to increase an electrical conductance through first conductor tip 110, the target tissue, and second conductor tip 110.

Illustratively, forceps arms 100 may be fixed within forceps arm housings wherein forceps arm proximal ends 102 are fixed within input conductor isolation mechanism 210 and forceps arm distal ends 101 are separated by a maximum conductor tip 110 separation distance. In one or more embodiments, a surgeon may decrease a distance between first forceps arm distal end 101 and second forceps arm distal end 101, e.g., by applying a force to a lateral portion of forceps arms 100. Illustratively, a surgeon may decrease a distance between first forceps arm distal end 101 and second forceps arm distal end 101, e.g., until first forceps arm distal end 101 contacts second forceps arm distal end 101. In one or more embodiments, a contact between first forceps arm distal end 101 and second forceps arm distal end 101 may be configured to electrically connect conductor tips 110. Illustratively, an electrical connection of conductor tips 110 may be configured to close an electrical circuit. In one or more embodiments, a surgeon may increase a distance between first forceps arm distal end 101 and second forceps arm distal end 101, e.g., by reducing a force applied to a lateral portion of forceps arms 100. Illustratively, increasing a distance between first forceps arm distal end 101 and second forceps arm distal end 101 may be configured to separate conductor tips 110. In one or more embodiments, a separation of conductor tips 110 may be configured to open an electrical circuit.

Figure 3A:
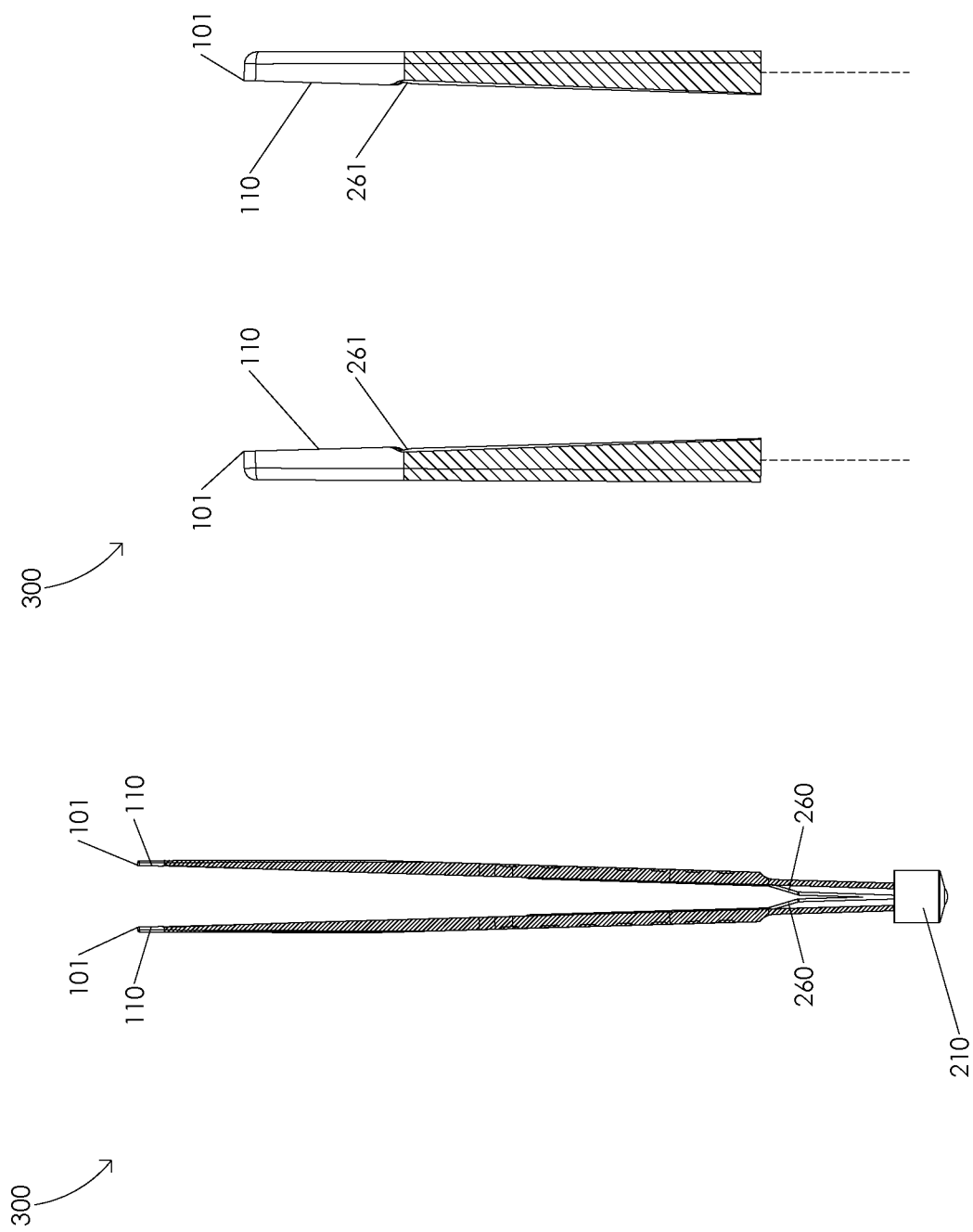

FIGS. 3A, 3B, 3C, 3D, and 3E are schematic diagrams illustrating a gradual closing of an irrigating bipolar forceps. FIG. 3A illustrates conductor tips in an open orientation 300. Illustratively, conductor tips 110 may comprise conductor tips in an open orientation 300, e.g., when forceps arm distal ends 101 are separated by a maximum conductor tip 110 separation distance. In one or more embodiments, forceps arm distal ends 101 may be separated by a distance in a range of 0.5 to 0.7 inches when conductor tips 110 comprise conductor tips in an open orientation 300, e.g., forceps arm distal ends 101 may be separated by a distance of 0.625 inches when conductor tips 110 comprise conductor tips in an open orientation 300. Illustratively, forceps arm distal ends 101 may be separated by a distance less than 0.5 inches or greater than 0.7 inches when conductor tips 110 comprise conductor tips in an open orientation 300. In one or more embodiments, conductor tips 110 may comprise conductor tips in an open orientation 300, e.g., when no force is applied to a lateral portion of forceps arms 100.

FIG. 3B illustrates conductor tips in a partially closed orientation 310. Illustratively, an application of a force to a lateral portion of forceps arms 100 may be configured to gradually close conductor tips 110 from conductor tips in an open orientation 300 to conductor tips in a partially closed orientation 310. In one or more embodiments, an application of a force to a lateral portion of forceps arms 100 may be configured to decrease a distance between first forceps arm distal end 101 and second forceps arm distal end 101. Illustratively, an application of a force having a magnitude in a range of 0.05 to 0.3 pounds to a lateral portion of forceps arms 100 may be configured to decrease a distance between first forceps arm distal end 101 and second forceps arm distal end 101, e.g., an application of a force having a magnitude of 0.2 pounds to a lateral portion of forceps arms 100 may be configured to decrease a distance between first forceps arm distal end 101 and second forceps arm distal end 101. In one or more embodiments, an application of a force having a magnitude less than 0.05 pounds or greater than 0.3 pounds to a lateral portion of forceps arms 100 may be configured to decrease a distance between first forceps arm distal end 101 and second forceps arm distal end 101. Illustratively, a decrease of a distance between first forceps arm distal end 101 and second forceps arm distal end 101 may be configured to decrease a distance between conductor tips 110. In one or more embodiments, an application of a force having a magnitude in a range of 0.05 to 0.3 pounds to a lateral portion of forceps arms 100 may be configured to gradually close conductor tips 110 from conductor tips in an open orientation 300 to conductor tips in a partially closed orientation 310. Illustratively, an application of a force having a magnitude less than 0.05 pounds or greater than 0.3 pounds to a lateral portion of forceps arms 100 may be configured to gradually close conductor tips 110 from conductor tips in an open orientation 300 to conductor tips in a partially closed orientation 310. In one or more embodiments, an amount of force applied to a lateral portion of forceps arms 100 configured to close conductor tips 110 to conductor tips in a partially closed orientation 310 and a total mass of an irrigating bipolar forceps may have a force applied to total mass ratio in a range of 1.25 to 8.75, e.g., an amount of force applied to a lateral portion of forceps arms 100 configured to close conductor tips 110 to conductor tips in a partially closed orientation 310 and a total mass of an irrigating bipolar forceps may have a force applied to total mass ratio of 5.25. Illustratively, an amount of force applied to a lateral portion of forceps arms 100 configured to close conductor tips 110 to conductor tips in a partially closed orientation 310 and a total mass of an irrigating bipolar forceps may have a force applied to total mass ratio less than 1.25 or greater than 8.75.

In one or more embodiments, a surgeon may dispose a tissue between a first forceps arm conductor tip 110 and a second forceps arm conductor tip 110, e.g., a surgeon may dispose a tumor tissue between a first forceps arm conductor tip 110 and a second forceps arm conductor tip 110. Illustratively, disposing a tissue between a first forceps arm conductor tip 110 and a second forceps arm conductor tip 110 may be configured to electrically connect the first forceps arm conductor tip 110 and the second forceps arm conductor tip 110, e.g., the tissue may electrically connect the first forceps arm conductor tip 110 and the second forceps arm conductor tip 110. In one or more embodiments, electrically connecting a first forceps arm conductor tip 110 and a second forceps arm conductor tip 110 may be configured to supply an electrical current to a tissue. Illustratively, supplying an electrical current to a tissue may be configured to coagulate the tissue, cauterize the tissue, ablate the tissue, etc. In one or more embodiments, electrically connecting a first forceps arm conductor tip 110 and a second forceps arm conductor tip 110 may be configured to seal a vessel, induce hemostasis, etc.

Illustratively, coagulating a tissue, cauterizing a tissue, ablating a tissue, sealing a vessel, or inducing hemostasis may be configured to increase a temperature of a first conductor tip 110. Increasing a temperature of a first conductor tip 110 may facilitate thermal spread to non-target tissue, e.g., increasing a temperature of a first conductor tip 110 may facilitate thermal spread to healthy tissue. Illustratively, an irrigation fluid may ingress a first fluid transport tube 260 at a first fluid transport tube proximal end 262. The irrigation fluid may flow through first fluid transport tube 260 and egress first fluid transport tube 260 at first fluid transport tube distal end 261. In one or more embodiments, irrigation fluid egressing first fluid transport tube 260 may be configured to reduce a temperature of a first conductor tip 110. Illustratively, reducing a temperature of a first conductor tip 110 may be configured to prevent thermal spread to a non-target tissue, e.g., reducing a temperature of a first conductor tip 110 may be configured to prevent thermal spread to healthy tissue. In one or more embodiments, coagulating a tissue, cauterizing a tissue, ablating a tissue, sealing a vessel, or inducing hemostasis may cause tissue to stick to a first conductor tip 110. Illustratively, irrigation fluid egressing first fluid transport tube 260 may be configured to prevent tissue from sticking to a first conductor tip 110.

Illustratively, coagulating a tissue, cauterizing a tissue, ablating a tissue, sealing a vessel, or inducing hemostasis may be configured to increase a temperature of a second conductor tip 110. Increasing a temperature of a second conductor tip 110 may facilitate thermal spread to non-target tissue, e.g., increasing a temperature of a second conductor tip 110 may facilitate thermal spread to healthy tissue. Illustratively, an irrigation fluid may ingress a second fluid transport tube 260 at a second fluid transport tube proximal end 262. The irrigation fluid may flow through second fluid transport tube 260 and egress second fluid transport tube 260 at second fluid transport tube distal end 261. In one or more embodiments, irrigation fluid egressing second fluid transport tube 260 may be configured to reduce a temperature of a second conductor tip 110. Illustratively, reducing a temperature of a second conductor tip 110 may be configured to prevent thermal spread to a non-target tissue, e.g., reducing a temperature of a second conductor tip 110 may be configured to prevent thermal spread to healthy tissue. In one or more embodiments, coagulating a tissue, cauterizing a tissue, ablating a tissue, sealing a vessel, or inducing hemostasis may cause tissue to stick to a second conductor tip 110. Illustratively, irrigation fluid egressing second fluid transport tube 260 may be configured to prevent tissue from sticking to a second conductor tip 110.

Illustratively, coagulating a tissue, cauterizing a tissue, ablating a tissue, sealing a vessel, or inducing hemostasis may be configured to increase a temperature of a first conductor tip 110 and increase a temperature of a second conductor tip 110. Increasing a temperature of a first conductor tip 110 and increasing a temperature of a second conductor tip 110 may facilitate thermal spread to non-target tissue, e.g., increasing a temperature of a first conductor tip 110 and increasing a temperature of a second conductor tip 110 may facilitate thermal spread to healthy tissue. Illustratively, an irrigation fluid may ingress a first fluid transport tube 260 at a first fluid transport tube proximal end 262 and a second fluid transport tube 260 at a second fluid transport tube proximal end 262. The irrigation fluid may flow through first fluid transport tube 260 and egress first fluid transport tube 260 at first fluid transport tube distal end 261 and the irrigation fluid may flow through second fluid transport tube 260 and egress second fluid transport tube 260 at second fluid transport tube distal end 261. In one or more embodiments, irrigation fluid egressing first fluid transport tube 260 may be configured to reduce a temperature of a first conductor tip 110 and irrigation fluid egressing second fluid transport tube 260 may be configured to reduce a temperature of a second conductor tip 110. Illustratively, reducing a temperature of a first conductor tip 110 and reducing a temperature of a second conductor tip 110 may be configured to prevent thermal spread to a non-target tissue, e.g., reducing a temperature of a first conductor tip 110 and reducing a temperature of a second conductor tip 110 may be configured to prevent thermal spread to healthy tissue. In one or more embodiments, coagulating a tissue, cauterizing a tissue, ablating a tissue, sealing a vessel, or inducing hemostasis may cause tissue to stick to a first conductor tip 110 and a second conductor tip 110. Illustratively, irrigation fluid egressing first fluid transport tube 260 may be configured to prevent tissue from sticking to a first conductor tip 110 and irrigation fluid egressing second fluid transport tube 260 may be configured to prevent tissue from sticking to a second conductor tip 110.

FIG. 3C illustrates conductor tips in a first closed orientation 320. Illustratively, an application of a force to a lateral portion of forceps arms 100 may be configured to gradually close conductor tips 110 from conductor tips in a partially closed orientation 310 to conductor tips in a first closed orientation 320. In one or more embodiments, an application of a force to a lateral portion of forceps arms 100 may be configured to decrease a distance between first forceps arm distal end 101 and second forceps arm distal end 101. Illustratively, a decrease of a distance between first forceps arm distal end 101 and second forceps arm distal end 101 may be configured to cause first forceps arm distal end 101 to contact second forceps arm distal end 101. In one or more embodiments, an application of a force having a magnitude in a range of 0.35 to 0.7 pounds to a lateral portion of forceps arms 100 may be configured to cause first forceps arm distal end 101 to contact second forceps arm distal end 101, e.g., an application of a force having a magnitude of 0.5 pounds to a lateral portion of forceps arms 100 may be configured to cause first forceps arm distal end 101 to contact second forceps arm distal end 101. Illustratively, an application of a force having a magnitude less than 0.35 pounds or greater than 0.7 pounds to a lateral portion of forceps arms 100 may be configured to cause first forceps arm distal end 101 to contact second forceps arm distal end 101. In one or more embodiment, an application of a force having a magnitude in a range of 0.35 to 0.7 pounds to a lateral portion of forceps arms 100 may be configured to gradually close conductor tips 110 from conductor tips in a partially closed orientation 310 to conductor tips in a first closed orientation 320. Illustratively, an application of a force having a magnitude less than 0.35 pounds or greater than 0.7 pounds to a lateral portion of forceps arms 100 may be configured to gradually close conductor tips 110 from conductor tips in a partially closed orientation 310 to conductor tips in a first closed orientation 320. In one or more embodiments, an amount of force applied to a lateral portion of forceps arms 100 configured to close conductor tips 110 to conductor tips in a first closed orientation 320 and a total mass of an irrigating bipolar forceps may have a force applied to total mass ratio in a range of 9.25 to 19.75, e.g., an amount of force applied to a lateral portion of forceps arms 100 configured to close conductor tips 110 to conductor tips in a first closed orientation 320 and a total mass of an irrigating bipolar forceps may have a force applied to total mass ratio of 13.65. Illustratively, an amount of force applied to a lateral portion of forceps arms 100 configured to close conductor tips 110 to conductor tips in a first closed orientation 320 and a total mass of an irrigating bipolar forceps may have a force applied to total mass ratio less than 9.25 or greater than 19.75.

In one or more embodiments, conductor tips 110 may comprise conductor tips in a first closed orientation 320, e.g., when first forceps arm distal end 101 contacts second forceps arm distal end 101 and no other portion of first forceps arm 100 contacts second forceps arm 100. Illustratively, conductor tips 110 may comprise conductor tips in a first closed orientation 320, e.g., when a distal end of a first forceps arm conductor tip 110 contacts a distal end of a second forceps arm conductor tip 110 and no other portion of first forceps arm 100 contacts second forceps arm 100. In one or more embodiments, first forceps arm conductor tip 110 and second forceps arm conductor tip 110 may have a contact area in a range of 0.0005 to 0.002 square inches when conductor tips 110 comprise conductor tips in a first closed orientation 320, e.g., first forceps arm conductor tip 110 and second forceps arm conductor tip 110 may have a contact area of 0.0016 square inches when conductor tips 110 comprise conductor tips in a first closed orientation 320. Illustratively, first forceps arm conductor tip 110 and second forceps arm conductor tip 110 may have a contact area of less than 0.0005 square inches or greater than 0.002 square inches when conductor tips 110 comprise conductor tips in a first closed orientation 320. In one or more embodiments, a proximal end of a first forceps arm conductor tip 110 may be separated from a proximal end of a second forceps arm conductor tip 110, e.g., when conductor tips 110 comprise conductor tips in a first closed orientation 320. Illustratively, a proximal end of a first forceps arm conductor tip 110 may be separated from a proximal end of a second forceps arm conductor tip 110 by a distance in a range of 0.005 to 0.015 inches when conductor tips 110 comprise conductor tips in a first closed orientation 320, e.g., a proximal end of a first forceps arm conductor tip 110 may be separated from a proximal end of a second forceps arm conductor tip 110 by a distance of 0.01 inches when conductor tips 110 comprise conductor tips in a first closed orientation 320. In one or more embodiments, a proximal end of a first forceps arm conductor tip 110 may be separated from a proximal end of a second forceps arm conductor tip 110 by a distance less than 0.005 inches or greater than 0.015 inches when conductor tips 110 comprise conductor tips in a first closed orientation 320.

Figure 3D:
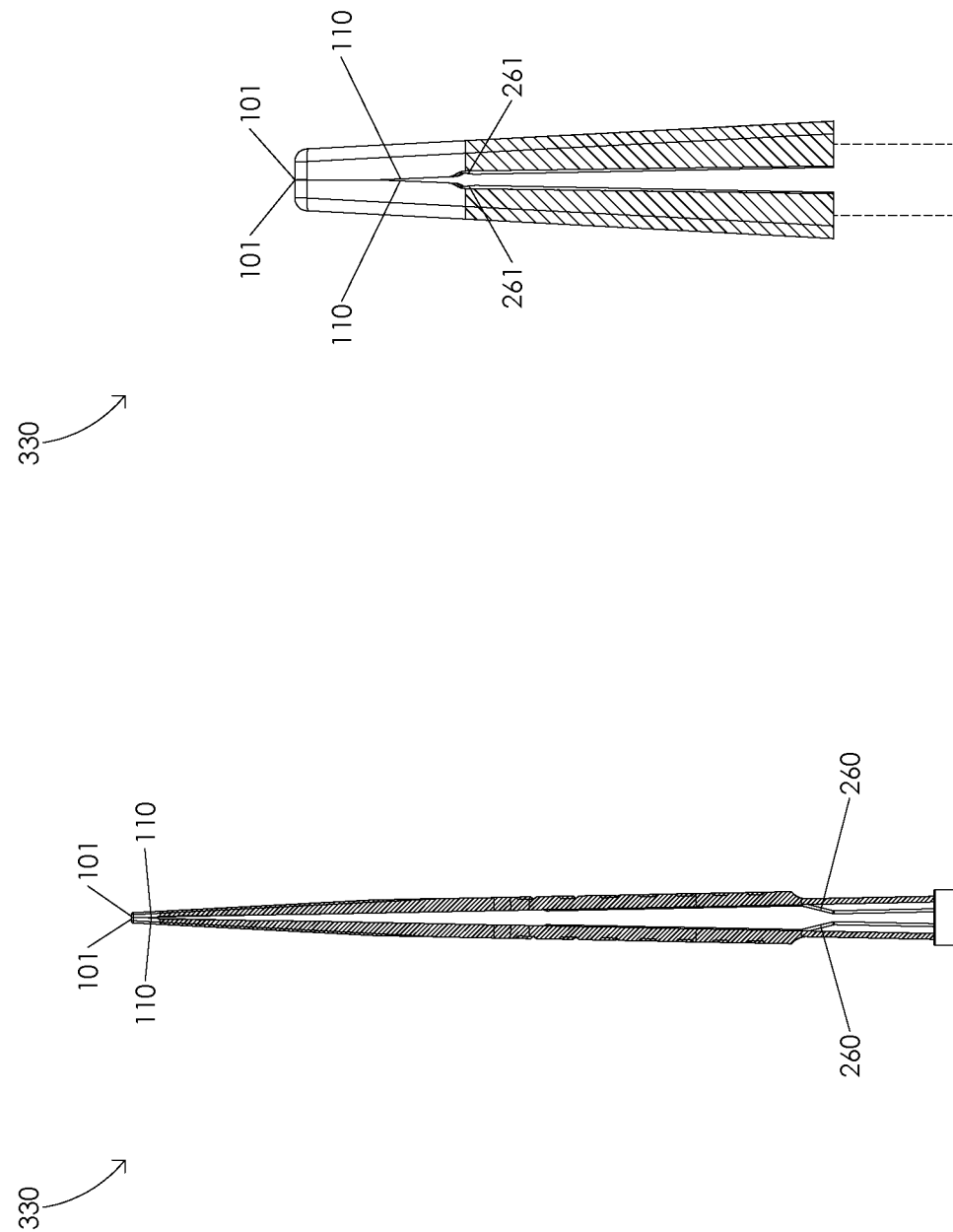

FIG. 3D illustrates conductor tips in a second closed orientation 330. Illustratively, an application of a force to a lateral portion of forceps arms 100 may be configured to gradually close conductor tips 110 from conductor tips in a first closed orientation 320 to conductor tips in a second closed orientation 330. In one or more embodiments, an application of a force to a lateral portion of forceps arms 100 may be configured to decrease a distance between a proximal end of first forceps arm conductor tip 110 and a proximal end of second forceps arm conductor tip 110. Illustratively, an application of a force to a lateral portion of forceps arms 100 may be configured to flex conductor tips in a first closed orientation 320, e.g., an application of a force to a lateral portion of forceps arms 100 may be configured to gradually increase a contact area between first forceps arm conductor tip 110 and second forceps arm conductor tip 110. In one or more embodiments, an application of a force having a magnitude in a range of 0.8 to 1.4 pounds to a lateral portion of forceps arms 100 may be configured to gradually increase a contact area between first forceps arm conductor tip 110 and second forceps arm conductor tip 110, e.g., an application of a force having a magnitude of 1.1 pounds to a lateral portion of forceps arms 100 may be configured to gradually increase a contact area between first forceps arm conductor tip 110 and second forceps arm conductor tip 110. Illustratively, an application of a force having a magnitude less than 0.8 pounds or greater than 1.4 pounds to a lateral portion of forceps arms 100 may be configured to gradually increase a contact area between first forceps arm conductor tip 110 and second forceps arm conductor tip 110. In one or more embodiments, an application of a force having a magnitude in a range of 0.8 to 1.4 pounds to a lateral portion of forceps arms 100 may be configured to gradually close conductor tips 110 from conductor tips in a first closed orientation 320 to conductor tips in a second closed orientation 330. Illustratively, an application of a force having a magnitude less than 0.8 pounds or greater than 1.4 pounds to a lateral portion of forceps arms 100 may be configured to gradually close conductor tips 110 from conductor tips in a first closed orientation 320 to conductor tips in a second closed orientation 330. In one or more embodiments, an amount of force applied to a lateral portion of forceps arms 100 configured to close conductor tips 110 to conductor tips in a second closed orientation 330 and a total mass of an irrigating bipolar forceps may have a force applied to total mass ratio in a range of 21.84 to 38.22, e.g., an amount of force applied to a lateral portion of forceps arms 100 configured to close conductor tips 110 to conductor tips in a second closed orientation 330 and a total mass of an irrigating bipolar forceps may have a force applied to total mass ratio of 30.03. Illustratively, an amount of force applied to a lateral portion of forceps arms 100 configured to close conductor tips 110 to conductor tips in a second closed orientation 330 and a total mass of an irrigating bipolar forceps may have a force applied to total mass ratio less than 21.84 or greater than 38.22.

In one or more embodiments, first forceps arm conductor tip 110 and second forceps arm conductor tip 110 may have a contact area in a range of 0.001 to 0.005 square inches when conductor tips 110 comprise conductor tips in a second closed orientation 330, e.g., first forceps arm conductor tip 110 and second forceps arm conductor tip 110 may have a contact area of 0.0025 square inches when conductor tips 110 comprise conductor tips in a second closed orientation 330. Illustratively, first forceps arm conductor tip 110 and second forceps arm conductor tip 110 may have a contact area less than 0.001 square inches or greater than 0.005 square inches when conductor tips 110 comprise conductor tips in a second closed orientation 330. In one or more embodiments, a proximal end of a first forceps arm conductor tip 110 may be separated from a proximal end of a second forceps arm conductor tip 110, e.g., when conductor tips 110 comprise conductor tips in a second closed orientation 330. Illustratively, a proximal end of a first forceps arm conductor tip 110 may be separated from a proximal end of a second forceps arm conductor tip 110 by a distance in a range of 0.001 to 0.0049 inches when conductor tips 110 comprise conductor tips in a second closed orientation 330, e.g., a proximal end of a first forceps arm conductor tip 110 may be separated from a proximal end of a second forceps arm conductor tip 110 by a distance of 0.0025 inches when conductor tips 110 comprise conductor tips in a second closed orientation 330. In one or more embodiments, a proximal end of a first forceps arm conductor tip 110 may be separated from a proximal end of a second forceps arm conductor tip 110 by a distance less than 0.001 inches or greater than 0.0049 inches when conductor tips 110 comprise conductor tips in a second closed orientation 330.

FIG. 3E illustrates conductor tips in a fully closed orientation 340. Illustratively, an application of a force to a lateral portion of forceps arms 100 may be configured to gradually close conductor tips 110 from conductor tips in a second closed orientation 330 to conductor tips in a fully closed orientation 340. In one or more embodiments, an application of a force to a lateral portion of forceps arms 100 may be configured to decrease a distance between a proximal end of first forceps arm conductor tip 110 and a proximal end of second forceps arm conductor tip 110. Illustratively, an application of a force to a lateral portion of forceps arms 100 may be configured to gradually increase a contact area between first forceps arm conductor tip 110 and second forceps arm conductor tip 110 until a proximal end of first forceps arm conductor tip 110 contacts a proximal end of second forceps arm conductor tip 110. In one or more embodiments, a proximal end of first forceps arm conductor tip 110 may contact a proximal end of second forceps arm conductor tip 110, e.g., when conductor tips 110 comprise conductor tips in a fully closed orientation 340. Illustratively, first forceps arm conductor tip 110 and second forceps arm conductor tip 110 may have a maximum contact area, e.g., when conductor tips 110 comprise conductor tips in a fully closed orientation 340. In one or more embodiments, first forceps arm conductor tip 110 and second forceps arm conductor tip 110 may have a contact area in a range of 0.01 to 0.015 square inches when conductor tips 110 comprise conductor tips in a fully closed orientation 340, e.g., first forceps arm conductor tip 110 and second forceps arm conductor tip 110 may have a contact area of 0.0125 square inches when conductor tips 110 comprise conductor tips in a fully closed orientation 340. Illustratively, first forceps arm conductor tip 110 and second forceps arm conductor tip 110 may have a contact area less than 0.01 square inches or greater than 0.015 square inches when conductor tips 110 comprise conductor tips in a fully closed orientation 340.

Illustratively, an application of a force having a magnitude in a range of 1.5 to 3.3 pounds to a lateral portion of forceps arms 100 may be configured to gradually close conductor tips 110 from conductor tips in a second closed orientation 330 to conductor tips in a fully closed orientation 340, e.g., an application of a force having a magnitude of 2.5 pounds to a lateral portion of forceps arms may be configured to gradually close conductor tips 110 from conductor tips in a second closed orientation 330 to conductor tips in a fully closed orientation 340. In one or more embodiments, an application of a force having a magnitude less than 1.5 pounds or greater than 3.3 pounds to a lateral portion of forceps arms 100 may be configured to gradually close conductor tips 110 from conductor tips in a second closed orientation 330 to conductor tips in a fully closed orientation 340. Illustratively, an amount of force applied to a lateral portion of forceps arms 100 configured to close conductor tips 110 to conductor tips in a fully closed orientation 340 and a total mass of a bipolar forceps may have a force applied to total mass ratio in a range of 40.95 to 90.10, e.g., an amount of force applied to a lateral portion of forceps arms 100 configured to close conductor tips 110 to conductor tips in a fully closed orientation 340 and a total mass of a bipolar forceps may have a force applied to total mass ratio of 68.26. In one or more embodiments, an amount of force applied to a lateral portion of forceps arms 100 configured to close conductor tips 110 to conductor tips in a fully closed orientation 340 and a total mass of a bipolar forceps may have a force applied to total mass ratio less than 40.95 or greater than 90.10.

Figure 4A:
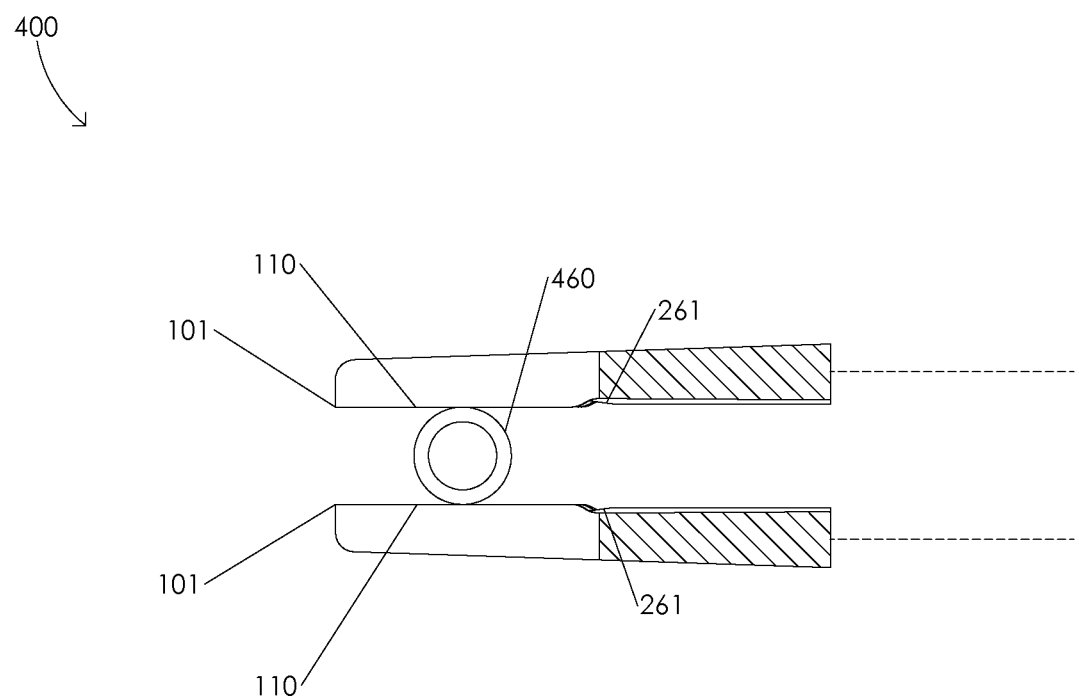
FIGS. 4A, 4B, and 4C are schematic diagrams illustrating a uniform compression of a vessel.
Figure 4B:
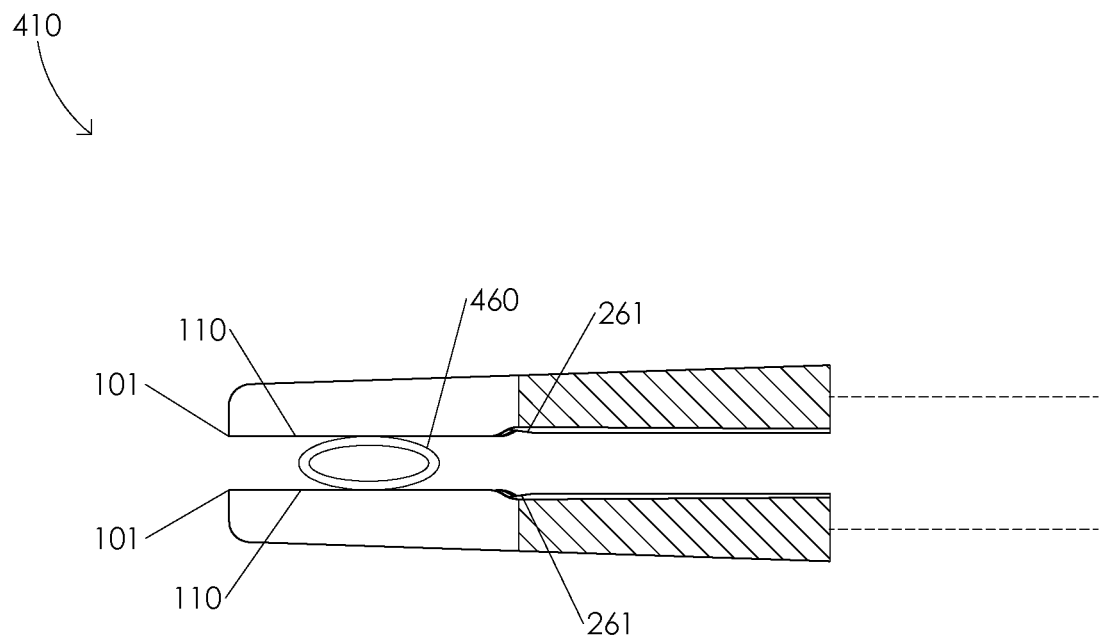
Figure 4C:
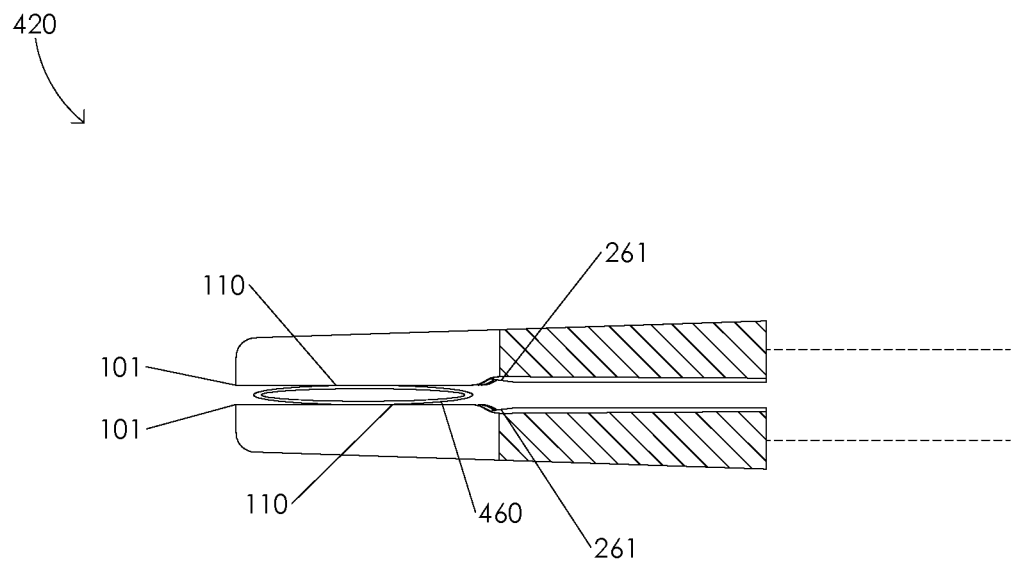

FIGS. 4A, 4B, and 4C are schematic diagrams illustrating a uniform compression of a vessel 460. In one or more embodiments, vessel 460 may comprise a blood vessel of an arteriovenous malformation. FIG. 4A illustrates an uncompressed vessel 400. Illustratively, vessel 460 may comprise an uncompressed vessel 400, e.g., when vessel 460 has a natural geometry. In one or more embodiments, vessel 460 may comprise an uncompressed vessel, e.g., when conductor tips 110 comprise conductor tips in a partially closed orientation 310. Illustratively, a surgeon may dispose vessel 460 between first forceps arm conductor tip 110 and second forceps arm conductor tip 110, e.g., when conductor tips 110 comprise conductor tips in an open orientation 300. In one or more embodiments, an application of a force to a lateral portion of forceps arms 100 may be configured to gradually close conductor tips 110 from conductor tips in an open orientation 300 to conductor tips in a partially closed orientation 310. Illustratively, vessel 460 may electrically connect first forceps arm conductor tip 110 and second forceps arm conductor tip 110, e.g., when vessel 460 comprises an uncompressed vessel 400. In one or more embodiments, a surgeon may identify an orientation of conductor tips 110 wherein conductor tips 110 initially contact vessel 460. Illustratively, a geometry of forceps arms 100 may be configured to allow a surgeon to visually identify an orientation of conductor tips 110 wherein conductor tips 110 initially contact vessel 460. In one or more embodiments, a mass of forceps arms 100 may be configured to allow a surgeon to tactilely identify an orientation of conductor tips 110 wherein conductor tips 110 initially contact vessel 460. Illustratively, a geometry of forceps arms 100 and a mass of forceps arms 100 may be configured to allow a surgeon to both visually and tactilely identify an orientation of conductor tips 110 wherein conductor tips 110 initially contact vessel 460.

FIG. 4B illustrates a partially compressed vessel 410. Illustratively, an application of a force to a lateral portion of forceps arms 100 may be configured to uniformly compress vessel 460 from an uncompressed vessel 400 to a partially compressed vessel 410. In one or more embodiments, an application of a force to a lateral portion of forceps arms 100 may be configured to uniformly increase a contact area between vessel 460 and forceps arm conductor tips 110. Illustratively, vessel 460 may electrically connect first forceps arm conductor tip 110 and second forceps arm conductor tip 110, e.g., when vessel 460 comprises a partially compressed vessel 410. In one or more embodiments, an application of a force to a lateral portion of forceps arms 100 may be configured to compress vessel 460 wherein vessel 460 maintains a symmetrical geometry with respect to a medial axis of vessel 460. Illustratively, vessel 460 may have a symmetrical geometry with respect to a medial axis of vessel 460 when vessel 460 comprises a partially compressed vessel 410. In one or more embodiments, conductor tips 110 may be configured to compress vessel 460 wherein no portion of vessel 460 is compressed substantially more than another portion of vessel 460, e.g., conductor tips 110 may be configured to evenly compress vessel 460 without pinching a first portion of vessel 460 or bulging a second portion of vessel 460. Illustratively, vessel 460 may be evenly compressed when vessel 460 comprises a partially compressed vessel 410.

FIG. 4C illustrates a fully compressed vessel 420. Illustratively, an application of a force to a lateral portion of forceps arms 100 may be configured to uniformly compress vessel 460 from a partially compressed vessel 410 to a fully compressed vessel 420. In one or more embodiments, an application of a force to a lateral portion of forceps arms 100 may be configured to uniformly increase a contact area between vessel 460 and forceps arm conductor tips 110. Illustratively, vessel 460 may electrically connect first forceps arm conductor tip 110 and second forceps arm conductor tip 110, e.g., when vessel 460 comprises a fully compressed vessel 420. In one or more embodiments, a surgeon may uniformly cauterize vessel 460, e.g., when vessel 460 comprises a fully compressed vessel 420. Illustratively, a surgeon may uniformly achieve hemostasis of vessel 460, e.g., when vessel 460 comprises a fully compressed vessel 420. In one or more embodiments, an application of a force to a lateral portion of forceps arms 100 may be configured to compress vessel 460 wherein vessel 460 maintains a symmetrical geometry with respect to a medial axis of vessel 460. Illustratively, vessel 460 may have a symmetrical geometry with respect to a medial axis of vessel 460 when vessel 460 comprises a fully compressed vessel 420. In one or more embodiments, conductor tips 110 may be configured to compress vessel 460 wherein no portion of vessel 460 is compressed substantially more than another portion of vessel 460, e.g., conductor tips 110 may be configured to evenly compress vessel 460 without pinching a first portion of vessel 460 or bulging a second portion of vessel 460. Illustratively, vessel 460 may be evenly compressed when vessel 460 comprises a fully compressed vessel 420.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a first forceps arm having a first forceps arm distal end and a first forceps arm proximal end;
   a first forceps arm grip of the first forceps arm having a first forceps arm grip distal end and a first forceps arm grip proximal end wherein the first forceps arm grip distal end is disposed between the first forceps arm distal end and the first forceps arm proximal end and wherein the first forceps arm grip proximal end is disposed between the first forceps arm distal end and the first forceps arm proximal end;
   a first conductor tip of the first forceps arm having a first conductor tip distal end and a first conductor tip proximal end;
   a first proximal channel of the first forceps arm having a first proximal channel distal end and a first proximal channel proximal end;
   a first distal channel of the first forceps arm having a first distal channel distal end and a first distal channel proximal end wherein the first distal channel proximal end is adjacent to the first proximal channel distal end and wherein the first distal channel distal end extends a distance in a range of 0.001 to 0.135 inches into the first conductor tip;
   a first fluid transport tube having a first fluid transport tube distal end and a first fluid transport tube proximal end, the first fluid transport tube disposed within the first proximal channel and the first distal channel wherein the first fluid transport tube distal end is adjacent to the first distal channel distal end;
   a first input conductor housing of the first forceps arm;
   a first coating of an electrical insulator material over at least a portion of the first forceps arm;
   a second forceps arm having a second forceps arm distal end and a second forceps arm proximal end, the second forceps arm disposed opposite the first forceps arm;
   a second forceps arm grip of the second forceps arm having a second forceps arm grip distal end and a second forceps arm grip proximal end, the second forceps arm grip disposed opposite the first forceps arm grip wherein the second forceps arm grip distal end is disposed between the second forceps arm distal and the second forceps arm proximal end and wherein the second forceps arm grip proximal end is disposed between the second forceps arm distal end and the second forceps arm proximal end;
   a second conductor tip of the second forceps arm having a second conductor tip distal end and a second conductor tip proximal end;

a second proximal channel of the second forceps arm having a second proximal channel distal end and a second proximal channel proximal end;

a second distal channel of the second forceps arm having a second distal channel distal end and a second distal channel proximal end wherein the second distal channel proximal end is adjacent to the second proximal channel distal end and wherein the second distal channel distal end extends a distance in a range of 0.001 to 0.135 inches into the second conductor tip;

a second input conductor housing of the second forceps arm;

a second coating of the electrical insulator material over at least a portion of the second forceps arm;

an input conductor isolation mechanism configured to electrically isolate the first input conductor housing of the first forceps arm and the second input conductor housing of the second forceps arm wherein the first forceps arm proximal end is disposed in the input conductor isolation mechanism and the second forceps arm proximal end is disposed in the input conductor isolation mechanism;

an irrigation tubing having an irrigation tubing distal end and an irrigation tubing proximal end, the irrigation tubing configured to contain an irrigation fluid;

an irrigation fluid multiplexer partially disposed within the irrigation tubing distal end wherein the irrigation fluid multiplexer is configured to increase an amount of the irrigation fluid directed into the first fluid transport tube in response to an increase in a temperature of the first conductor tip;

an irrigation supply adaptor configured to interface with an irrigation supply system, the irrigation supply adaptor at least partially disposed within the irrigation tubing proximal end;

a conduction zone defined between the first conductor tip and the second conductor tip;

wherein the instrument is configured to conduct current through an electrical circuit of the first forceps arm, the first conductor tip, the conduction zone, the second conductor tip, and the second forceps arm; and wherein the first fluid transport tube proximal end is disposed within the irrigation fluid multiplexer.

2. The instrument of claim 1 wherein a surface of the first conductor tip has a roughness average in a range of 25.0 to 150.0 nanometers.

3. The instrument of claim 1 wherein a surface of the first conductor tip has a root mean square average between height deviations over a total surface of the first conductor tip in a range of 30.0 to 150.0 nanometers.

4. The instrument of claim 1 wherein a surface of the first conductor tip has a maximum height difference between a highest point and a lowest point of a total surface area of the first conductor tip in a range of 200.0 to 1300.0 nanometers.

5. The instrument of claim 1 wherein the first proximal channel has a diameter in a range of 1.25 to 1.75 millimeters.

6. The instrument of claim 1 wherein the first proximal channel has a depth in a range of 0.035 to 0.040 inches.

7. The instrument of claim 1 wherein the first proximal channel has a surface area in a range of 0.5 to 0.8 square inches.

8. The instrument of claim 1 wherein the first proximal channel has a volume in a range of 0.015 to 0.025 cubic inches.

9. The instrument of claim 1 wherein the first distal channel has a diameter in a range of 0.75 to 1.25 millimeters.

10. The instrument of claim 1 wherein the first distal channel has a depth in a range of 0.035 to 0.040 inches.

11. The instrument of claim 1 wherein the first distal channel has a surface area in a range of 0.04 to 0.08 square inches.

12. The instrument of claim 1 wherein the first distal channel has a volume in a range of 0.0005 to 0.0015 cubic inches.

13. The instrument of claim 1 further comprising:

a second fluid transport tube having a second fluid transport tube distal end and a second fluid transport tube proximal end, the second fluid transport tube disposed within the second proximal channel and the second distal channel wherein the second fluid transport tube distal end is adjacent to the second distal channel distal end and wherein the second fluid transport tube proximal end is disposed within the irrigation fluid multiplexer.

14. The instrument of claim 1 further comprising:

a bipolar cord; and an electrosurgical generator adaptor of the bipolar cord.

15. An instrument comprising:

a first forceps arm having a first forceps arm distal end and a first forceps arm proximal end;

a first forceps arm grip of the first forceps arm having a first forceps arm grip distal end and a first forceps arm grip proximal end wherein the first forceps arm grip distal end is disposed between the first forceps arm distal end and the first forceps arm proximal end and wherein the first forceps arm grip proximal end is disposed between the first forceps arm distal end and the first forceps arm proximal end;

a first conductor tip of the first forceps arm having a first conductor tip distal end and a first conductor tip proximal end;

a first proximal channel of the first forceps arm having a first proximal channel distal end and a first proximal channel proximal end;

a first distal channel of the first forceps arm having a first distal channel distal end and a first distal channel proximal end wherein the first distal channel proximal end is adjacent to the first proximal channel distal end and wherein the first distal channel distal end extends a distance into the first conductor tip;

a first fluid transport tube having a first fluid transport tube distal end and a first fluid transport tube proximal end, the first fluid transport tube disposed within the first proximal channel and the first distal channel wherein the first fluid transport tube distal end is adjacent to the first distal channel distal end;

a first input conductor housing of the first forceps arm;

a first coating of an electrical insulator material over at least a portion of the first forceps arm;

a second forceps arm having a second forceps arm distal end and a second forceps arm proximal end, the second forceps arm disposed opposite the first forceps arm;

a second forceps arm grip of the second forceps arm having a second forceps arm grip distal end and a second forceps arm grip proximal end, the second forceps arm grip disposed opposite the first forceps arm grip wherein the second forceps arm grip distal end is disposed between the second forceps arm distal and the second forceps arm proximal end and wherein the second forceps arm grip proximal end is disposed between the second forceps arm distal end and the second forceps arm proximal end;

a second conductor tip of the second forceps arm having a second conductor tip distal end and a second conductor tip proximal end;
a second proximal channel of the second forceps arm having a second proximal channel distal end and a second proximal channel proximal end;
a second distal channel of the second forceps arm having a second distal channel distal end and a second distal channel proximal end wherein the second distal channel proximal end is adjacent to the second proximal channel distal end and wherein the second distal channel distal end extends a distance into the second conductor tip;
a second fluid transport tube having a second fluid transport tube distal end and a second fluid transport tube proximal end, the second fluid transport tube disposed within the second proximal channel and the second distal channel wherein the second fluid transport tube distal end is adjacent to the second distal channel distal end;
a second input conductor housing of the second forceps arm;
a second coating of the electrical insulator material over at least a portion of the second forceps arm;
an input conductor isolation mechanism configured to electrically isolate the first input conductor housing of the first forceps arm and the second input conductor housing of the second forceps arm wherein the first forceps arm proximal end is disposed in the input conductor isolation mechanism and the second forceps arm proximal end is disposed in the input conductor isolation mechanism;
an irrigation tubing having an irrigation tubing distal end and an irrigation tubing proximal end, the irrigation tubing configured to contain an irrigation fluid;
an irrigation fluid multiplexer partially disposed within the irrigation tubing distal end wherein the irrigation fluid multiplexer is configured to increase an amount of the irrigation fluid directed into the first fluid transport tube in response to an increase in a temperature of the first conductor tip;
a conduction zone defined between the first conductor tip and the second conductor tip;
wherein the instrument is configured to conduct current through an electrical circuit of the first forceps arm, the first conductor tip, the conduction zone, the second conductor tip, and the second forceps arm; and
wherein the first fluid transport tube proximal end is disposed within the irrigation fluid multiplexer.

16. An instrument comprising:
a first forceps arm having a first forceps arm distal end and a first forceps arm proximal end;
a first forceps arm grip of the first forceps arm having a first forceps arm grip distal end and a first forceps arm grip proximal end wherein the first forceps arm grip distal end is disposed between the first forceps arm distal end and the first forceps arm proximal end and wherein the first forceps arm grip proximal end is disposed between the first forceps arm distal end and the first forceps arm proximal end;
a first conductor tip of the first forceps arm having a first conductor tip distal end and a first conductor tip proximal end;
a first proximal channel of the first forceps arm having a first proximal channel distal end and a first proximal channel proximal end;
a first distal channel of the first forceps arm having a first distal channel distal end and a first distal channel proximal end wherein the first distal channel proximal end is adjacent to the first proximal channel distal end and wherein the first distal channel distal end extends a distance in a range of 0.001 to 0.135 inches into the first conductor tip;
a first fluid transport tube having a first fluid transport tube distal end and a first fluid transport tube proximal end, the first fluid transport tube disposed within the first proximal channel and the first distal channel wherein the first fluid transport tube distal end is adjacent to the first distal channel distal end;
a first input conductor housing of the first forceps arm;
a first coating of an electrical insulator material over at least a portion of the first forceps arm;
a second forceps arm having a second forceps arm distal end and a second forceps arm proximal end, the second forceps arm disposed opposite the first forceps arm;
a second forceps arm grip of the second forceps arm having a second forceps arm grip distal end and a second forceps arm grip proximal end, the second forceps arm grip disposed opposite the first forceps arm grip wherein the second forceps arm grip distal end is disposed between the second forceps arm distal and the second forceps arm proximal end and wherein the second forceps arm grip proximal end is disposed between the second forceps arm distal end and the second forceps arm proximal end;
a second conductor tip of the second forceps arm having a second conductor tip distal end and a second conductor tip proximal end;
a second proximal channel of the second forceps arm having a second proximal channel distal end and a second proximal channel proximal end;
a second distal channel of the second forceps arm having a second distal channel distal end and a second distal channel proximal end wherein the second distal channel proximal end is adjacent to the second proximal channel distal end and wherein the second distal channel distal end extends a distance in a range of 0.001 to 0.135 inches into the second conductor tip;
a second input conductor housing of the second forceps arm;
a second coating of the electrical insulator material over at least a portion of the second forceps arm;
an input conductor isolation mechanism configured to electrically isolate the first input conductor housing of the first forceps arm and the second input conductor housing of the second forceps arm wherein the first forceps arm proximal end is disposed in the input conductor isolation mechanism and the second forceps arm proximal end is disposed in the input conductor isolation mechanism;
an irrigation tubing having an irrigation tubing distal end and an irrigation tubing proximal end, the irrigation tubing configured to contain an irrigation fluid;
an irrigation fluid multiplexer configured to control a flow of the irrigation fluid wherein the irrigation fluid multiplexer is partially disposed within the irrigation tubing distal end;
an irrigation tubing having an irrigation tubing distal end and an irrigation tubing proximal end, the irrigation tubing configured to contain an irrigation fluid; and
an irrigation fluid multiplexer partially disposed within the irrigation tubing distal end wherein the irrigation fluid multiplexer is configured to increase an amount of the irrigation fluid directed into the first fluid transport tube in response to an increase in a temperature of the first conductor tip;

an irrigation supply adaptor configured to interface with an irrigation supply system, the irrigation supply adaptor at least partially disposed within the irrigation tubing proximal end;

a conduction zone defined between the first conductor tip and the second conductor tip;

wherein the instrument is configured to conduct current through an electrical circuit of the first forceps arm, the first conductor tip, the conduction zone, the second conductor tip, and the second forceps arm; and wherein the first fluid transport tube proximal end is disposed within the irrigation fluid multiplexer.

* * * * *